United States Patent
Frydman et al.

US007491849B2

(10) Patent No.: US 7,491,849 B2
(45) Date of Patent: Feb. 17, 2009

(54) OLIGOAMINE COMPOUNDS AND DERIVATIVES THEREOF FOR CANCER THERAPY

(75) Inventors: Benjamin Frydman, Madison, WI (US); Linda Clifford, legal representative, Madison, WI (US); Aldonia L. Valasinas, Buenos Aires (AR); Andrei V. Blokhin, Madison, WI (US); Hirak S. Basu, Madison, WI (US); Laurence J. Marton, Palo Alto, CA (US); Venodhar K. Reddy, Madison, WI (US)

(73) Assignee: Progen Pharmaceuticals, Inc., Redwood City, CA (US)

( * ) Notice: Subject to any disclaimer, the term of this patent is extended or adjusted under 35 U.S.C. 154(b) by 0 days.

(21) Appl. No.: 10/957,105

(22) Filed: Oct. 1, 2004

(65) Prior Publication Data

US 2005/0080144 A1    Apr. 14, 2005

Related U.S. Application Data

(63) Continuation of application No. 10/272,269, filed on Oct. 16, 2002, now abandoned.

(60) Provisional application No. 60/329,982, filed on Oct. 16, 2001.

(51) Int. Cl.
*C07C 211/13* (2006.01)
*A61K 31/13* (2006.01)

(52) U.S. Cl. ........................... 564/512; 514/674

(58) Field of Classification Search ................. None
See application file for complete search history.

(56) References Cited

U.S. PATENT DOCUMENTS

| | | | |
|---|---|---|---|
| 2,440,724 A | 5/1948 | Morey |
| 3,956,502 A | 5/1976 | Slovinsky et al. |
| 4,013,507 A | 3/1977 | Rembaum |
| 4,551,550 A | 11/1985 | Bey |
| 4,661,509 A | 4/1987 | Gordon et al. |
| 4,868,219 A | 9/1989 | Thornfeldt |
| 4,889,851 A | 12/1989 | Oku et al. |
| 4,971,598 A | 11/1990 | Andress et al. |
| 5,091,576 A | 2/1992 | Bergeron |
| 5,132,425 A | 7/1992 | Sotoya et al. |
| 5,185,369 A | 2/1993 | Saccomano et al. |
| 5,242,684 A | 9/1993 | Merianos |
| 5,283,367 A | 2/1994 | Babiarz et al. |
| 5,393,757 A | 2/1995 | Bergeron, Jr. et al. |
| 5,512,597 A | 4/1996 | Kyba et al. |
| 5,530,092 A | 6/1996 | Meijer et al. |
| 5,599,847 A | 2/1997 | Robins et al. |
| 5,627,215 A | 5/1997 | Frei et al. |
| 5,650,099 A | 7/1997 | Akhavan-Tafti et al. |
| 5,654,484 A | 8/1997 | Prakash et al. |
| 5,677,351 A | 10/1997 | Bergeron, Jr. |
| 5,698,662 A | 12/1997 | Stoelwinder et al. |
| 5,710,153 A | 1/1998 | Ohmoto et al. |
| 5,719,193 A | 2/1998 | Bowlin et al. |
| 5,736,297 A | 4/1998 | Roeschert et al. |
| 5,750,788 A | 5/1998 | Haussling et al. |
| 5,824,812 A | 10/1998 | Nantz et al. |
| 5,843,865 A | 12/1998 | Del Corral et al. |
| 5,847,190 A | 12/1998 | Paulus et al. |
| 5,866,016 A | 2/1999 | Jaquess et al. |
| 5,880,161 A | 3/1999 | Basu et al. |
| 5,886,050 A | 3/1999 | Bergeron, Jr. |
| 5,886,051 A | 3/1999 | Bergeron, Jr. et al. |
| 5,906,996 A | 5/1999 | Murphy |
| 5,932,201 A | 8/1999 | de Labbey et al. |
| 5,958,397 A | 9/1999 | Smerbeck et al. |
| 5,962,533 A | 10/1999 | Bergeron, Jr. |
| 6,034,129 A | 3/2000 | Mandeville, III et al. |
| 6,046,282 A | 4/2000 | Starner et al. |
| 6,051,611 A | 4/2000 | Kyba et al. |
| 6,068,835 A | 5/2000 | Franzke et al. |
| 6,103,666 A | 8/2000 | Del Corral et al. |
| 6,184,232 B1 | 2/2001 | Bergeron, Jr. et al. |
| 6,235,794 B1 | 5/2001 | Bergeron, Jr. |
| 6,274,630 B1 | 8/2001 | Bergeron, Jr. |
| 6,307,102 B1 | 10/2001 | Tokumoto et al. |
| 6,319,956 B1 | 11/2001 | Iwata |
| 6,342,534 B1 | 1/2002 | Bergeron, Jr. |
| 6,384,097 B1 | 5/2002 | Tokumoto et al. |
| 6,384,177 B1 | 5/2002 | Tokumoto et al. |
| 6,399,662 B1 | 6/2002 | Bergeron |
| 6,444,707 B1 | 9/2002 | Lampe et al. |
| 6,528,048 B1 | 3/2003 | Koike et al. |
| 6,531,512 B1 | 3/2003 | Kramer et al. |
| 6,605,645 B2 | 8/2003 | Iwata |
| 6,641,655 B1 | 11/2003 | McElhinney et al. |
| 6,649,587 B1 | 11/2003 | Frydman et al. |
| 6,664,270 B2 | 12/2003 | Bergeron, Jr. |
| 6,673,890 B1 | 1/2004 | Boeckh et al. |
| RE38,417 E | 2/2004 | Bergeron, Jr. |

(Continued)

FOREIGN PATENT DOCUMENTS

CA    2321200 A1    9/1999

(Continued)

OTHER PUBLICATIONS

Database, CAPLUS on STN, Acc. No. 1971:143260, Saito et al., JP 45030077 (Sep. 30, 1970) (abstract).*

(Continued)

*Primary Examiner*—Brian J Davis
(74) *Attorney, Agent, or Firm*—Morrison & Foerster LLP

(57) ABSTRACT

Oligoamine compounds with anti-cancer and anti-proliferative activity are provided, as well as methods for making and using the compounds. The compounds are shown to be active against prostate cancer cell lines and against prostate cancer tumors in mice. The compounds are also useful in treatment of breast cancer and other cancers.

21 Claims, 2 Drawing Sheets

U.S. PATENT DOCUMENTS

| | | | |
|---|---|---|---|
| 6,706,922 | B2 | 3/2004 | Wolff et al. |
| 2002/0045780 | A1 | 4/2002 | Bergeron, Jr. |
| 2002/0061287 | A1 | 5/2002 | Wolff et al. |
| 2002/0061926 | A1 | 5/2002 | Phillips |
| 2002/0094990 | A1 | 7/2002 | Bergeron |
| 2002/0143068 | A1 | 10/2002 | Bergeron, Jr. |
| 2003/0045674 | A1 | 3/2003 | Higley |
| 2003/0055113 | A1 | 3/2003 | Wang et al. |
| 2003/0100615 | A1 | 5/2003 | Bergeron, Jr. |
| 2003/0130356 | A1 | 7/2003 | Frydman et al. |
| 2003/0130534 | A1 | 7/2003 | Golden |
| 2003/0143713 | A1 | 7/2003 | Aghajari et al. |
| 2003/0158262 | A1 | 8/2003 | Ramesh et al. |
| 2003/0185778 | A1 | 10/2003 | Fahl et al. |
| 2003/0232799 | A1 | 12/2003 | Wang et al. |
| 2004/0006055 | A1 | 1/2004 | Winchell |
| 2004/0019043 | A1 | 1/2004 | Coucouvanis et al. |
| 2004/0019087 | A1 | 1/2004 | Ternansky et al. |
| 2004/0039057 | A1 | 2/2004 | Perlmutter et al. |
| 2004/0047844 | A1 | 3/2004 | Shepard |
| 2004/0133013 | A1 | 7/2004 | Frydman et al. |
| 2005/0233943 | A1 | 10/2005 | Frydman et al. |

FOREIGN PATENT DOCUMENTS

| | | |
|---|---|---|
| CS | 252771 | 10/1987 |
| EP | 0 186 473 A2 | 7/1986 |
| EP | 0 186 473 A3 | 7/1986 |
| EP | 0 723 772 A1 | 7/1996 |
| EP | 0 889 112 A1 | 1/1999 |
| JP | 45-030077 B | 9/1970 |
| JP | 07-228589 A2 | 8/1995 |
| JP | 07-277964 A2 | 10/1995 |
| JP | 2000-026320 A2 | 1/2000 |
| JP | 2001-131449 A2 | 5/2001 |
| PL | 109 855 B1 | 6/1980 |
| WO | WO-93/04036 A1 | 3/1993 |
| WO | WO-94/07480 A1 | 4/1994 |
| WO | WO-95/18091 A1 | 7/1995 |
| WO | WO-95/20580 A1 | 8/1995 |
| WO | WO-96/38528 A1 | 12/1996 |
| WO | WO-97/07674 A1 | 3/1997 |
| WO | WO-98/14190 A1 | 4/1998 |
| WO | WO-98/17624 A1 | 4/1998 |
| WO | WO-98/51660 A1 | 11/1998 |
| WO | WO-99/17802 A1 | 4/1999 |
| WO | WO-99/43752 A1 | 9/1999 |
| WO | WO-99/54283 A1 | 10/1999 |
| WO | WO-00/09634 A1 | 2/2000 |
| WO | WO-00/18969 A1 | 4/2000 |
| WO | WO-00/66175 A2 | 11/2000 |
| WO | WO-00/66175 A3 | 11/2000 |
| WO | WO-01/64779 A2 | 9/2001 |
| WO | WO-01/79329 A1 | 10/2001 |
| WO | WO-02/22584 A1 | 3/2002 |
| WO | WO-02/38105 A2 | 5/2002 |
| WO | WO-02/38105 A3 | 5/2002 |
| WO | WO-02/062341 A1 | 8/2002 |
| WO | WO-02/091989 A2 | 11/2002 |
| WO | WO-02/091989 A3 | 11/2002 |
| WO | WO-03/033455 A1 | 4/2003 |

OTHER PUBLICATIONS

Database CAPLUS on STN, Acc. No. 1990:164044, Urbanek et al., CS 252771 (Oct. 15, 1987) (abstract).*

Arago, J. et al. (1992). "Macrocyclic Effect on Anion binding. A Potentiometric and Electrochemical Study of the Interaction of 21- and 24-Membered Polyazaalkanes with $[Fe(CN_6)]^{4-}$ and $[Co(CN_6)]^{3-}$," J. Chem Soc. Dalton Trans, pp. 319-324.

Bacchi, C.J. et al. (2001). "SL-11158, A Synthetic Oligoamine, Inhibits Polyamine Metabolism of Encephalitozoon cunicull", J. Eukaryot. Microbiol., pp. 92S-94S.

Bacchi, C.J. et al. (Jan. 2002). "Novel Synthetic Polyamines Are Effective in the Treatment of Experimental Microsporidiosis, an Opportunistic AIDS-Associated Infection", Antimicrobial Agents And Chemotherapy 46(1):55-61.

Baker, L.A. et al. (2002). "Synthesis and Catalytic Properties of Imidazole-Functionalized Poly(propylene imine) Dendrimers," Bulletin Of The Korean Chemical Society 23(5):647-654.

Bazzicalupi, C. et al. (1998). "Palladium (II) Co-ordination by Linear N-methylated Polyamines: A Solution and Solid-State Study," J. Chem. Soc. Dalton Trans., pp. 1625-1631.

Bruice, T.C. et al. (1997). "A Microgonotropen Branched Decaaza Decabutylamine and its DNA and DNA/Transcription Factor Interactions," Biorganic & Medicinal Chemistry 5(4):685-692.

Cabani, S.et al. (1999). "Molecular Dioxygen Binding to Co(H) Complexes With Open-Chain and Macrocyclic Polyazaalkanes in Aqueous Solutions,"Annali Di Chimica (Societa chimica Italiana) 89:99-106.

CAPlus Abstract of CS252771—Chemical Abstracts Accession No. 112:164044 (1990:164044), (1990).

CAPlus Abstract of JP 45-30077—Chemical Abstracts Accession No. 74:143260 (1971:143260), (1971).

Casero, R.A., Jr. et al. (Dec. 28, 2000). "Terminally Alkylated Polyamine Analogues as Chemotherapeutic Agents," J. Med. Chem. 44(1):1-26.

Database CAPLUS on STN, Acc. No. 1986:517956, EP 186473 (Jul. 2, 1986) (abstract).

Derwent World Patent Index Abstract of WO 99/43752, (1999).

Dubowchik, G.M., et al. (1996). "A Lipophilic Polyamino-Bolaamphiphile Designed to Dissipate pH Gradients Across a Bilayer Membrane: Synthesis and Proton Transport," Tetrahedron Letters 37(36):6465-6468.

Frydman, B. et al. (1999). "Polyamine-Based Chemotherapy of Cancer," Exp. Opin. Ther. Patents 9(8):1055-1068.

Krakowiak, K.E. et al. (1996). "Thermal Removal of Boc-Protecting Groups During Preparation of Open-Chain Polyamines," Synthetic Communications 26(21):3999-4004.

Kröger, N. et al. (Dec. 19, 2000). "Species-Specific Polyamines From Diatoms Control Silica Morphology", Proc. Natl. Acad. Sci. USA 97(26):14133-14138.

Lange, P. et al. (1996). "Dendrimer-Based Multinuclear Gold (I) Complexes," Inorg. Chem. 35:637-642.

Mitchell, J.L.A. et al. (2002). "Antizyme Induction by Polyamine Analogues as a Factor of Cell Growth Inhibition," Biochem. J. 366:663-671.

Sakai, N. et al. (1997). "Transmembrane Ion Transport Mediated by Amphiphilic Polyamine Dendrimers," Tetrahedron Letters 38(15):2613-2616.

Salmon, A. et al. (2001). "Water Soluble Ferrocenyl and Polyferrocenyl Compounds: Synthesis and Electrochemistry," Journal Of Organometallic Chemistry 637-639:595-608.

Satz, A.L. et al. (2002). "Recognition in the Minor Groove of Double-Stranded DNA by Microgonotropens," Accounts Of Chemical Research 35(2):86-95.

Tasaki, K. et al. (2001). "Computer Simulation of $LiPF_6$ Salt Association in Li-Ion Battery Electrolyte in the Presence of an Anion Trapping Agent," Journal Of The Electrochemical Society 148(9):A984-A988.

Tsiourvas, D. et al. (2002). "Liquid Crystals Derived from Cholesterol Functionalized Poly(propylene imine) Dendrimers," Macromolecules 35:6466-6469.

Office Action mailed Oct. 20, 2005 for U.S. Appl. No. 10/970,089 filed Oct. 20, 2004, nine pages.

Chemical Abstracts CAPLUS and Registry records for CS 252771, 8 pages, (1987).

Chemical Abstracts CAPLUS and Registry records for JP 45-030077, 3 pages, (2000).

CAPLUS Abstract of PL 109855—Chemical Abstracts Accession No. 98:43002 (1983:43002), five pages, (1984).

* cited by examiner

Effect of SL-11159 cytotoxicity in PC-3 cells after 5 days incubation.

OLIGOAMINE COMPOUNDS AND DERIVATIVES THEREOF FOR CANCER THERAPY

CROSS-REFERENCE TO RELATED APPLICATIONS

This application is a continuation of U.S. application Ser. No. 10/272,269, filed Oct. 16, 2002 now abandoned, which claims priority benefit of U.S. provisional patent application Ser. No. 60/329,982, filed Oct. 16, 2001. The entire contents of those applications are hereby incorporated herein by reference.

STATEMENT OF RIGHTS TO INVENTIONS MADE UNDER FEDERALLY SPONSORED RESEARCH

Not applicable.

TECHNICAL FIELD

This invention is directed to compounds and methods useful for treating cancer and other diseases caused by uncontrolled cell proliferation, and for treating microsporidiosis and other infectious diseases. More specifically, this invention is directed to oligoamine compounds which display anti-tumor activity in vitro and in vivo, and which display anti-microspora activity as well as methods of making and using those compounds.

BACKGROUND ART

Cancer is one of the leading causes of death in the world. According to the World Health Organization, cancer is the third most common cause of death in the world, after heart disease and infectious disease. Cancer is the second most common cause of death (after heart disease) in the developed world. Accordingly, discovery of new and effective treatments for cancer is a high priority for health care researchers.

Cancer is often treated by using chemotherapy to selectively kill or hinder the growth of cancer cells, while having a less deleterious effect on normal cells. Chemotherapeutic agents often kill rapidly dividing cells, such as cancer cells; cells which are dividing less rapidly are affected to a lesser degree. Other agents, such as antibodies attached to toxic agents, have been evaluated for use against cancers. These agents target the cancer cells by making use of a characteristic specific to the cancer, for example, higher-than-normal rates of cell division, or unique antigens expressed on the cancer cell surface.

Various naturally-occurring and synthetic amine-containing compounds have been evaluated for anti-cancer and anti-proliferative activity. The following patents and patent applications, all of which are hereby incorporated by reference in their entirety, discuss certain of these compounds: U.S. Pat. Nos. 5,541,230, 5,880,161, and 5,889,061; and International Patent Cooperation Treaty Applications WO 00/66587, WO 98/17624, and WO 95/18091. Other publications which discuss various amine-containing compounds, for a wide variety of applications, include U.S. Pat. No. 3,956,502, to polyamine alcohols as microbicides; U.S. Pat. No. 4,013,507 and U.S. Pat. No. 5,866,016, which relate to the compounds commonly called ionenes; CA 2,231,200, which discusses polyalkylimines as gene transport carriers; EP 889 112, directed to a lubricating oil composition for automatic transmissions; U.S. Pat. No. 4,971,598, directed to reaction products of alkenyl succinimides with ethylenediamine carboxy acids as fuel detergents; U.S. Pat. No. 5,091,576, which discusses anti-neoplastic, anti-viral, or anti-retroviral spermine derivatives, and U.S. Pat. No. 5,393,757, which discusses polyamines and anti-diarrheal and gastrointestinal anti-spasmodic pharmaceutical compositions and methods of treatment; WO 93/04036 and U.S. Pat. No. 5,185,369, directed to synthetic aryl and heteroaryl polyamines as excitatory amino acid neurotransmitter antagonists; U.S. Pat. No. 5,530,092 and U.S. Pat. No. 5,698,662, directed to dendritic macromolecules and the preparation thereof; U.S. Pat. No. 5,750,788, which discusses preparation of amines from compounds having at least three cyano groups; U.S. Pat. No. 5,847,190, to dendritic nitrogen-containing organic compounds; U.S. Pat. No. 6,046,282, to reactive diluents for polyamidoamine epoxy curatives; WO 95/20580, to macrocyclic octaaza compounds; WO 96/38528, directed to betaine esters for the delivery of alcohols; WO 97/07674, WO 98/51660, and WO 99/17802, to ethyleneimine oligomers for selective modification of nucleic acids; WO 00/09634, to diesel fuels comprising hydrocarbyl amines; WO 01/64779, to polyamine polyoxides used as asphalt emulsifiers; WO 01/79329, to oligopolysuccinimides; Bruice TC et al., "A microgonotropen branched decaaza decabutylamine and its DNA and DNA/transcription factor interactions," Bioorg Med Chem. 5(4):685-92 (1997); Satz AL and Bruice TC, "Recognition in the minor groove of double-stranded DNA by microgonotropens: Acc. Chem. Res. 35(2):86-95 (2002); Kroger N et al., "Species-specific polyamines from diatoms control silica morphology," Proc. Natl. Acad. Sci. USA 97(26):14133-8 (2000); Bacchi CJ et al., "Novel synthetic polyamines are effective in the treatment of experimental microsporidiosis, an opportunistic AIDS-associated infection," Antimicrob. Agents Chemother. 46(1):55-61 (2002); and Bacchi CJ et al., "SL-11158, a synthetic oligoamine, inhibits polyamine metabolism of *Encephalitozoon cuniculi*," J. Eukaryot. Microbiol. Suppl:92S-94S (2001).

Despite intensive research aimed at finding effective treatments for cancer, is well-known that, while some cancers can be treated with relative success, no effective treatments exist for other cancers. Thus, there is a need for additional pharmaceutical agents to complement the medicinal remedies currently available for treatment of cancer and diseases characterized by uncontrolled cell proliferation.

In addition to treatment of cancer, the oligoamine compounds of the present invention are also useful for treatment of diseases caused by microorganisms such as bacteria, viruses, and parasites. See Bacchi CJ et al., "Novel synthetic polyamines are effective in the treatment of experimental microsporidiosis, an opportunistic AIDS-associated infection," Antimicrob. Agents Chemother. 46(1):55-61 (2002); and Bacchi CJ et al., "SL-11158, a synthetic oligoamine, inhibits polyamine metabolism of *Encephalitozoon cuniculi*," J. Eukaryot. Microbiol. Suppl:92S-94S (2001). Microsporidiosis refers to infections caused by any of the parasitic protists of the phylum Microspora; over 140 genera and 1200 species of microsporidia are known, and at least 14 of these species can cause pathology in humans: *Enterocytozoon bieneusi, Encephalitozoon intestinalis* (previously known as *Septata intestinalis*), *Encephalitozoon hellem, Encephalitozoon cuniculi, Pleistophora* sp., *Trachipleistophora hominis, T. anthropophthera, Nosema ocularum, N. algerae, Vittaforma corneae, Microsporidium ceylonensis, M. africanum, Brachiola vesicularum,* and *B. connori*. (See Centers for Disease Control information at World Wide Web URL www.dpd.cdc.gov/dpdx/HTML/Microsporidiosis.htm). Microsporidiosis is most prevalent in immunocompromised hosts, such as patients with AIDS and HIV-related diseases, or transplant recipients on immunosuppressive therapy. Healthy hosts appear to harbor asymptomatic or self-limiting microsporidiosis. Symptoms of microsporidiosis include diarrhea and other gastrointestinal complications, muscle infections, genitourinary infections, respiratory infections, and eye infections.

While pharmaceutical treatments currently exist for microsporidiosis, such as albendazole and metronidazole (Flagyl), not all treatments are effective against every pathogen, and undesirable side effects to specific medicines can occur in certain individuals. Thus, additional medicinal agents are needed to complement the treatments currently available for microsporidiosis and other diseases caused by microbes.

DISCLOSURE OF THE INVENTION

The invention is directed to oligoamine compounds and derivatives thereof, methods of making them, and methods of using them.

In particular, the invention embraces compounds of the formula:

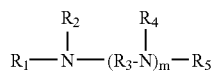

where $R_1$ is independently selected from the group consisting of H and $C_1$-$C_4$ linear alkyl; $R_2$ is independently selected from the group consisting of H and $C_1$-$C_4$ linear alkyl; each $R_3$ is independently selected from the group consisting of $C_1$-$C_8$ linear alkyl; each $R_4$ is independently selected from the group consisting of H and $C_1$-$C_4$ linear alkyl; $R_5$ is independently selected from the group consisting of H and $C_1$-$C_4$ linear alkyl; m is an integer between 7 and 15, inclusive; and all salts thereof.

In one embodiment, $R_1$ is H. In another embodiment, $R_2$ is H. In another embodiment, both $R_1$ and $R_2$ are H.

In another embodiment, at least one of $R_5$ and the $R_4$ moiety bonded to the nitrogen to which $R_5$ is also bonded is H. In another embodiment, both $R_5$ and the $R_4$ moiety bonded to the nitrogen to which $R_5$ is also bonded are H. In another embodiment, each $R_4$ is H. In another embodiment, $R_1$ is ethyl.

In another embodiment, $R_1$ is ethyl and $R_2$ is H. In another embodiment, $R_5$ is ethyl. In another embodiment, $R_5$ is ethyl and the $R_4$ moiety bonded to the nitrogen to which $R_5$ is also bonded is H.

In another embodiment, $R_1$ is ethyl, $R_2$ is H, $R_5$ is ethyl and the $R_4$ moiety bonded to the nitrogen to which $R_5$ is also bonded is H.

In yet another embodiment, each $R_3$ is independently selected from the group consisting of $C_3$-$C_4$ linear alkyl. In yet another embodiment, each $R_3$ is $C_3$ linear alkyl. In yet another embodiment, each $R_3$ is $C_4$ linear alkyl.

In other embodiments, m is 7. In other embodiments, m is 9. In other embodiments, m is 11. In other embodiments, m is 13. In other embodiments, m is 15.

The invention also embraces compounds of the formula:

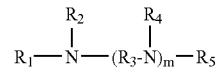

where $R_1$ is independently selected from the group consisting of H and $C_1$-$C_4$ linear alkyl; $R_2$ is independently selected from the group consisting of H and $C_1$-$C_4$ linear alkyl; each $R_3$ is independently selected from the group consisting of $C_1$-$C_8$ linear hydroxyalkyl and $C_1$-$C_8$ linear alkyl, with the proviso that at least one $R_3$ is $C_1$-$C_8$ linear hydroxyalkyl; each $R_4$ is independently selected from the group consisting of H and $C_1$-$C_4$ linear alkyl; $R_5$ is independently selected from the group consisting of H and $C_1$-$C_4$ linear alkyl; m is an integer between 7 and 15, inclusive; and all salts thereof.

In one embodiment, at least one of $R_1$ and $R_2$ is H. In another embodiment, both $R_1$ and $R_2$ are H. In another embodiment, at least one of $R_5$ and the $R_4$ moiety bonded to the nitrogen to which $R_5$ is also bonded is H. In another embodiment, each $R_4$ is H.

In another embodiment, $R_1$ is ethyl. In another embodiment, $R_1$ is ethyl and $R_2$ is H. In another embodiment, $R_5$ is ethyl. In another embodiment, $R_5$ is ethyl and the $R_4$ moiety bonded to the nitrogen to which $R_5$ is also bonded is H.

In another embodiment, $R_1$ is ethyl, $R_2$ is H, $R_5$ is ethyl and the $R_4$ moiety bonded to the nitrogen to which $R_5$ is also bonded is H.

In yet another embodiment, each $R_3$ is independently selected from the group consisting of $C_3$-$C_4$ linear hydroxyalkyl and $C_3$-$C_4$ linear alkyl, with the proviso that at least one $R_3$ is $C_3$-$C_4$ linear hydroxyalkyl. In yet another embodiment, each $R_3$ is independently selected from $C_3$ linear hydroxyalkyl and $C_3$ linear alkyl, with the proviso that at least one $R_3$ is $C_3$ linear hydroxyalkyl. In yet another embodiment, each $R_3$ is independently selected from $C_4$ linear hydroxyalkyl and $C_4$ linear alkyl, with the proviso that at least one $R_3$ is $C_4$ linear hydroxyalkyl.

In other embodiments, m is 7. In other embodiments, m is 9. In other embodiments, m is 11. In other embodiments, m is 13. In other embodiments, m is 15.

In additional embodiments, the alkyl segment flanked by the two leftmost nitrogens of the compound contains a hydroxyalkyl group. In additional embodiments, the alkyl segment flanked by the two leftmost nitrogens of the compound contains the only hydroxyalkyl group in the molecule. That is, when the structure is drawn out in its entirety, the first $R_3$ group encountered when reading left to right is a hydroxyalkyl group, or the only hydroxyalkyl group. In additional embodiments, the alkyl segment flanked by the two rightmost nitrogens of the compound contains a hydroxyalkyl group. In additional embodiments, the alkyl segment flanked by the two rightmost nitrogens of the compound contains the only hydroxyalkyl group in the molecule. That is, when the structure is drawn out in its entirety, the last $R_3$ group encountered when reading left to right is a hydroxyalkyl group, or the only hydroxyalkyl group.

In another embodiment, the invention embraces compounds of the formula:

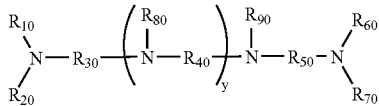

where $R_{10}$, $R_{20}$, $R_{60}$, and $R_{70}$ are independently selected from H, methyl, ethyl, n-propyl, isopropyl, n-butyl, isobutyl, sec-butyl, and t-butyl;

where each $R_{80}$ and $R_{90}$ are independently selected from H, methyl, ethyl, n-propyl, isopropyl, n-butyl, isobutyl, sec-butyl, and t-butyl;

where $R_{30}$, each $R_{40}$, and $R_{50}$ are independently selected from:

—$CH_2CH_2CH_2CH_2$—
—$CHOHCH_2CH_2CH_2$—
—$CH_2CHOHCH_2CH_2$—
—$CH_2CH_2CHOHCH_2$—
—$CH_2CH_2CH_2CHOH$—
—$CH_2CH_2CH_2$—
—$CHOHCH_2CH_2$—
—$CH_2CHOHCH_2$—
—$CH_2CH_2CHOH$;— and where y is an integer selected from 5, 6, 7, 8, 9, 10, 11, 12, and 13; and all salts thereof.

In one embodiment, at least one $R_{30}$, $R_{40}$, or $R_{50}$ is independently selected from:

—$CHOHCH_2CH_2CH_2$—
—$CH_2CHOHCH_2CH_2$—
—$CH_2CH_2CHOHCH_2$—
—$CH_2CH_2CH_2CHOH$—
—$CHOHCH_2CH_2$—
—$CH_2CHOHCH_2$— and
—$CH_2CH_2CHOH$—.

In another embodiment, at least one $R_{30}$, $R_{40}$, or $R_{50}$ is independently selected from:

—$CHOHCH_2CH_2CH_2$—
—$CH_2CHOHCH_2CH_2$—
—$CH_2CH_2CHOHCH_2$—; and
—$CH_2CH_2CH_2CHOH$—.

In another embodiment, at least one of $R_{30}$ and $R_{50}$ is independently selected from:

—$CHOHCH_2CH_2CH_2$—
—$CH_2CHOHCH_2CH_2$—
—$CH_2CH_2CHOHCH_2$—; and
—$CH_2CH_2CH_2CHOH$—.

In another embodiment, each $R_{40}$ is independently selected from the group consisting of —$CH_2CH_2CH_2$— and —$CH_2CH_2CH_2CH_2$—. In another embodiment, $R_{30}$ is independently selected from the group consisting of —$CH_2CH_2CH_2$— and —$CH_2CH_2CH_2CH_2$—. In another embodiment, $R_{50}$ is independently selected from the group consisting of —$CH_2CH_2CH_2$— and —$CH_2CH_2CH_2CH_2$—. In another embodiment, $R_{30}$ and $R_{50}$ are independently selected from the group consisting of —$CH_2CH_2CH_2$— and —$CH_2CH_2CH_2CH_2$—. In another embodiment, $R_{40}$ and $R_{50}$ are independently selected from the group consisting of —$CH_2CH_2CH_2$— and —$CH_2CH_2CH_2CH_2$—. In another embodiment, $R_{30}$ and $R_{40}$ are independently selected from the group consisting of —$CH_2CH_2CH_2$— and —$CH_2CH_2CH_2CH_2$—. In another embodiment, $R_{30}$, each $R_{40}$, and $R_{50}$ are independently selected from the group consisting of —$CH_2CH_2CH_2$— and —$CH_2CH_2CH_2CH_2$—. In one embodiment of the foregoing embodiments, y=5, 7, 9, 11, or 13. In yet another embodiment, y=6, 8, 10, or 12. In yet another embodiment, y=5, 7, 9, or 11. In yet another embodiment, y=5. In yet another embodiment, y=7. In yet another embodiment, y=9. In yet another embodiment, y=11.

In another embodiment, each $R_{40}$ is —$CH_2CH_2CH_2CH_2$—. In another embodiment, $R_{30}$ is —$CH_2CH_2CH_2CH_2$—. In another embodiment, $R_{50}$ is —$CH_2CH_2CH_2CH_2$—. In another embodiment, $R_{30}$ and $R_{50}$ are —$CH_2CH_2CH_2CH_2$—. In another embodiment, each $R_{40}$ and $R_{50}$ are —$CH_2CH_2CH_2CH_2$—. In another embodiment, $R_{30}$ and each $R_{40}$ are —$CH_2CH_2CH_2CH_2$—. In another embodiment, $R_{30}$, each $R_{40}$, and $R_{50}$ are —$CH_2CH_2CH_2CH_2$—. In one embodiment of the foregoing embodiments, y=5, 7, 9, 11, or 13. In yet another embodiment, y=6, 8, 10, or 12. In yet another embodiment, y=5, 7, 9, or 11. In yet another embodiment, y=5. In yet another embodiment, y=7. In yet another embodiment, y=9. In yet another embodiment, y=11.

In another embodiment, each $R_{40}$ is —$CH_2CH_2CH_2$—. In another embodiment, $R_{30}$ is —$CH_2CH_2CH_2$—. In another embodiment, $R_{50}$ is —$CH_2CH_2CH_2$—. In another embodiment, $R_{30}$ and $R_{50}$ are —$CH_2CH_2CH_2$—. In another embodiment, each $R_{40}$ and $R_{50}$ are —$CH_2CH_2CH_2$—. In another embodiment, $R_{30}$ and each $R_{40}$ are —$CH_2CH_2CH_2$—. In another embodiment, $R_{30}$, each $R_{40}$, and $R_{50}$ are —$CH_2CH_2CH_2$—. In one embodiment of the foregoing embodiments, y=5, 7, 9, 11, or 13. In yet another embodiment, y=6, 8, 10, or 12. In yet another embodiment, y=5, 7, 9, or 11. In yet another embodiment, y=5. In yet another embodiment, y=7. In yet another embodiment, y=9. In yet another embodiment, y=11.

In one embodiment, $R_{10}$, $R_{20}$, $R_{60}$, and $R_{70}$ are independently selected from H, methyl, ethyl, n-propyl, and n-butyl. In another embodiment, each $R_{80}$ and $R_{90}$ are independently selected from H, methyl, ethyl, n-propyl, and n-butyl. In another embodiment, $R_{10}$, $R_{20}$, $R_{60}$, and $R_{70}$ are independently selected from H, methyl, ethyl, n-propyl, and n-butyl, and each $R_{80}$ and $R_{90}$ are independently selected from H, methyl, ethyl, n-propyl, and n-butyl.

In another embodiment, $R_{90}$ and each $R_{80}$ are H. In another embodiment, $R_{10}$ is H, $R_{20}$ is ethyl, $R_{60}$ is H, and $R_{70}$ is ethyl. In one embodiment of the foregoing embodiments, y=5, 7, 9, 11, or 13. In yet another embodiment, y=6, 8, 10, or 12. In yet another embodiment, y=5, 7, 9, or 11. In yet another embodiment, y=5. In yet another embodiment, y=7. In yet another embodiment, y=9. In yet another embodiment, y=11.

In another embodiment, $R_{30}$, each $R_{40}$, and $R_{50}$ are —$CH_2CH_2CH_2CH_2$—, and $R_{90}$ and each $R_{80}$ are H. In another embodiment, $R_{30}$, each $R_{40}$, and $R_{50}$ are —$CH_2CH_2CH_2CH_2$—, and $R_{10}$ is H, $R_{20}$ is ethyl, $R_{60}$ is H, and $R_{70}$ is ethyl. In another embodiment, $R_{30}$, each $R_{40}$, and $R_{50}$ are —$CH_2CH_2CH_2CH_2$—, $R_{90}$ and each $R_{80}$ are H, and $R_{10}$ is H, $R_{20}$ is ethyl, $R_{60}$ is H, and $R_{70}$ is ethyl. In one embodiment of the foregoing embodiments, y=5, 7, 9, 11, or 13. In yet another embodiment, y=6, 8, 10, or 12. In yet another embodiment, y=5, 7, 9, or 11. In yet another embodiment, y=5. In yet another embodiment, y=7. In yet another embodiment, y=9. In yet another embodiment, y=11.

In another embodiment, the invention embraces compounds of the formula: $CH_3CH_2NHCH_2CH_2CH_2CH_2(NHCH_2CH_2CH_2CH_2)_yNHCH_2CH_2CH_2CH_2NHCH_2CH_3$ where y=5, 6, 7, 8, 9, 10, 11, 12, or 13. In yet another embodiment, y=5, 7, 9, 11, or 13. In yet another embodiment, y=6, 8, 10, or 12. In yet another embodiment, y=5, 7, 9, or 11. In yet another embodiment, y=5. In yet another embodiment, y=7. In yet another embodiment, y=9. In yet another embodiment, y=11.

In another embodiment, the invention embraces compounds of the formula: $CH_3CH_2NHCH_2CH_2CH_2(NHCH_2CH_2CH_2)_yNHCH_2CH_2CH_2NHCH_2CH_3$ where y=5, 6, 7, 8, 9, 10, 11, 12, or 13. In yet another embodiment, y=5, 7, 9, 11, or 13. In yet another embodiment, y=6, 8, 10, or 12. In yet another embodiment, y=5, 7, 9, or 11. In yet another embodiment, y=5. In yet another embodiment, y=7. In yet another embodiment, y=9. In yet another embodiment, y=11.

In another embodiment, the invention embraces the compounds $CH_3CH_2$—NH—$(CH_2CH_2CH_2CH_2$—NH—$)_9$—$CH_2CH_3$, $CH_3CH_2$—NH—$(CH_2CH_2CH_2CH_2$—NH—$)_7$—$CH_2CH_3$, $CH_3CH_2$—NH—$(CH_2CH_2CH_2CH_2$—NH—$)_{13}$—$CH_2CH_3$, and $CH_3CH_2$—NH—$(CH_2CH_2CH_2CH_2$—NH—$)_{11}$—$CH_2CH_3$, and all salts thereof.

The invention also embraces methods of making the compounds described above, by protecting the amino group of an alkylamine in such a manner that it can undergo one, and only one, alkylation reaction at the amino group (such as protection with mesitylenesulfonyl chloride), reacting the protected alkylamine with a haloalkylnitrile compound, reducing the nitrile group to an amino group, repeating the protection, reaction, and reduction steps as desired until the desired chain length is generated, and optionally reacting the last nitrogen to be added with an alkyl halide to terminate the synthesis.

The invention also embraces methods of making the compounds by preparing a linear amide chain, where the linear amide chain is formed by protecting the nitrogen of an ω-amino acid, reacting the carboxyl group of the protected ω-amino acid with an alkylamine to form an amino-protected ω-amino amide; deprotecting the amino group of the ω-amino amide; and reacting the amino group of the ω-amino amide with the carboxyl group of a second ω-amino acid to form a peptide bond. This latter reaction can be repeated as desired until the desired chain length is reached. The final nitrogen added to the polyamide compound can optionally be reacted with an alkanoic acid. Finally, the polyamide compound can be reduced to a polyamine compound.

In another embodiment, the invention also embraces a method of making a compound

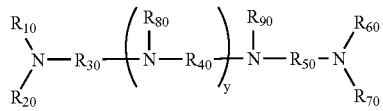

where $R_{10}$, $R_{20}$, $R_{30}$, $R_{40}$, $R_{50}$, $R_{60}$, $R_{70}$, $R_{80}$, and $R_{90}$ are as defined in the various embodiments above, comprising the steps of:

a) providing a first compound of the form

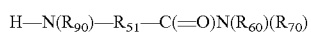

where $R_{51}$ is selected from the group consisting of
—$CH_2CH_2CH_2$—
—$CHO(PG_{Hy})CH_2CH_2$—
—$CH_2CHO(PG_{Hy})CH_2$—
—$CH_2CH_2CHO(PG_{Hy})$-
—$CH_2CH_2$—
—$CHO(PG_{Hy})CH_2$— and
—$CH_2CHO(PG_{Hy})$- where $PG_{Hy}$ is a hydroxy protecting group;

b) providing a second compound of the form

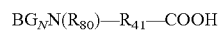

where blocking group $BG_N$ is selected from the group consisting of an amino protecting group and methyl, ethyl, n-propyl, isopropyl, n-butyl, isobutyl, sec-butyl, and t-butyl; $R_{80}$ is as defined in the various embodiments above; $R_{41}$ is selected from the group consisting of
—$CH_2CH_2CH_2$—
—$CHO(PG_{Hy})CH_2CH_2$—
—$CH_2CHO(PG_{Hy})CH_2$—
—$CH_2CH_2CHO(PG_{Hy})$-
—$CH_2CH_2$—
—$CHO(PG_{Hy})CH_2$— and
—$CH_2CHO(PG_{Hy})$-;

c) activating the carboxyl group of the second compound;
d) coupling the second compound to the first compound to form a compound of the formula

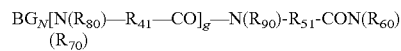

where g is 1;
e) repeating step c) and repeating the coupling step of step d) for (g-1) additional cycles to form a compound of the formula

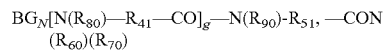

where g is an integer from 7 to 15;
f) reducing the amide groups to amine groups; and
g) removing any protecting groups $BG_N$ and $PG_{Hy}$ that may be present in the compound. The resulting compound may optionally be purified by any method known in the art, such as column chromatography, ion-exchange chromatography, HPLC, or thin-layer chromatography.

The invention also provides methods of treating diseases characterized by uncontrolled cell proliferation, such as cancer, including, but not limited to, prostate cancer and breast cancer, by administration of one or more of the compounds described above. The invention also includes compositions of one or more of the compounds described above in combination with a pharmaceutically-acceptable carrier, and/or with another therapeutic agent. Examples of compounds of the invention which can be used for the treatment of diseases characterized by uncontrolled cell proliferation, e.g. cancer, such as prostate cancer and breast cancer, are $CH_3CH_2$—NH—$(CH_2CH_2CH_2CH_2$—NH—$)_9$—$CH_2CH_3$, $CH_3CH_2$—NH—$(CH_2CH_2CH_2CH_2$—NH—$)_7$—$CH_2CH_3$, $CH_3CH_2$—NH—$(CH_2CH_2CH_2CH_2$—NH—$)_{13}$—$CH_2CH_3$, or $CH_3CH_2$—NH—$(CH_2CH_2CH_2CH_2$—NH—$)_{11}$—$CH_2CH_3$, or any salt thereof.

The invention also embraces a method of treating microsporidiosis and AIDS-associated infections, by administration of one or more of the compounds described above.

BEST MODE FOR CARRYING OUT THE INVENTION

Figure 1:
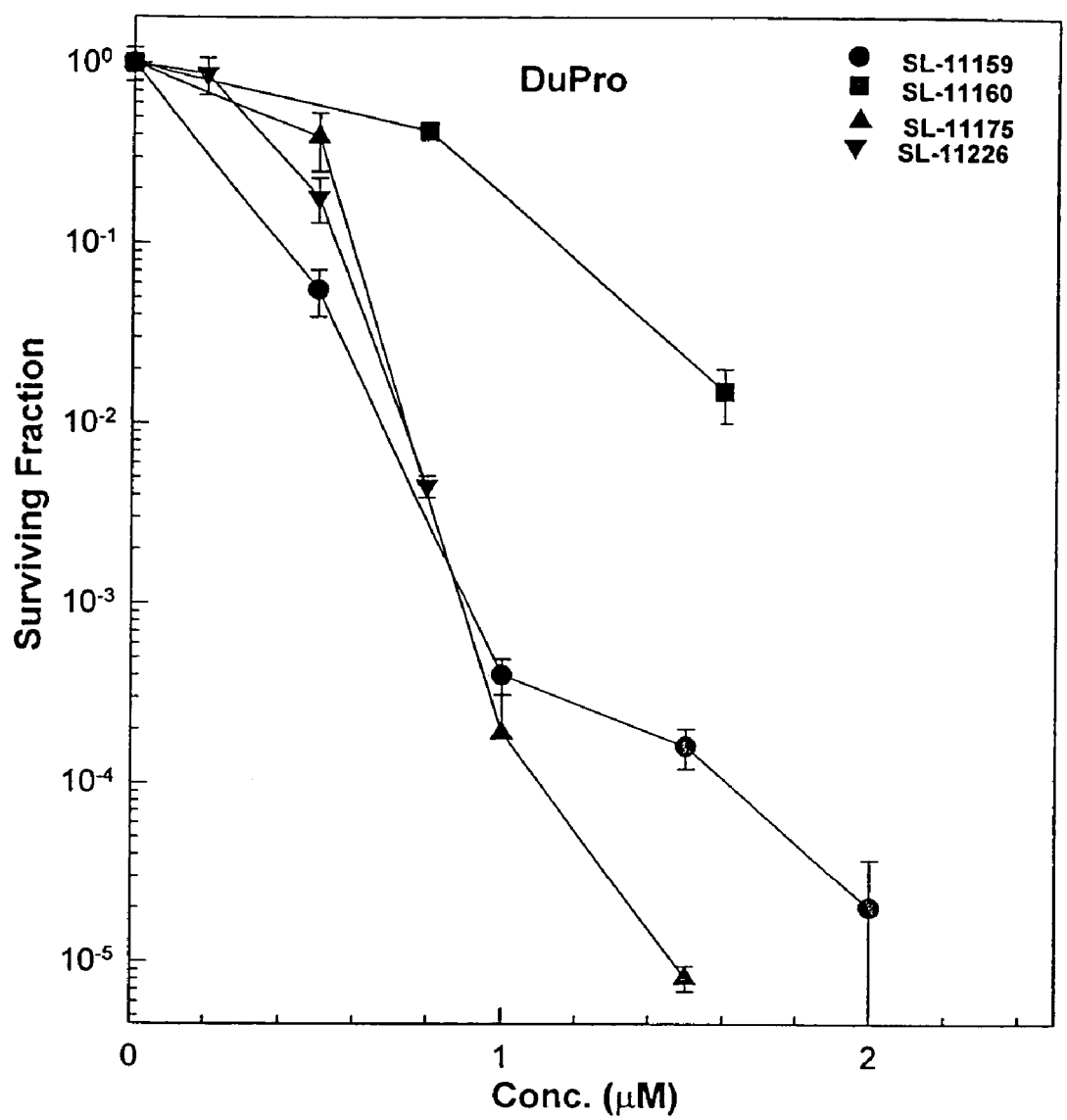
FIG. 1 depicts the effects of SL-11159, SL-11160, SL-11175, and SL-11226 on survival of DuPro cancer cells.

The invention is directed to various novel oligoamine compounds and derivatives thereof as described herein. The invention includes all salts of the compounds described herein. Particularly preferred are pharmaceutically acceptable salts. Pharmaceutically acceptable salts are those salts which retain the biological activity of the free bases and which are not biologically or otherwise undesirable. The desired salt may be prepared by methods known to those of skill in the art by treating the polyamine with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of the polyamines with amino acids, such as aspartate salts and glutamate salts, can also be prepared.

The invention also includes all stereoisomers of the compounds, including diastereomers and enantiomers, as well as mixtures of stereoisomers, including, but not limited to, racemic mixtures. Unless stereochemistry is explicitly indicated in a structure, the structure is intended to embrace all possible stereoisomers of the compound depicted.

The term "alkyl" refers to saturated aliphatic groups including straight-chain, branched-chain, cyclic groups, and combinations thereof, having the number of carbon atoms specified, or if no number is specified, having up to 12 carbon atoms. "Straight-chain alkyl" or "linear alkyl" groups refers to alkyl groups that are neither cyclic nor branched, commonly designated as "n-alkyl" groups. Examples of alkyl groups include, but are not limited to, groups such as methyl, ethyl, n-propyl, isopropyl, n-butyl, isobutyl, sec-butyl, t-butyl, n-pentyl, neopentyl, cyclopropyl, cyclobutyl, cyclopentyl, cyclohexyl, and adamantyl. Cyclic groups can consist of one ring, including, but not limited to, groups such as cycloheptyl, or multiple fused rings, including, but not limited to, groups such as adamantyl or norbornyl.

"Substituted alkyl" refers to alkyl groups substituted with one or more substituents including, but not limited to, groups such as halogen (fluoro, chloro, bromo, and iodo), alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of substituted alkyl groups include, but are not limited to, —$CF_3$, —$CF_2$—$CF_3$, and other perfluoro and perhalo groups.

"Hydroxyalkyl" specifically refers to alkyl groups having the number of carbon atoms specified substituted with one —OH group. Thus, "$C_3$ linear hydroxyalkyl" refers to —$CH_2CH_2CHOH$—, —$CH_2CHOHCH_2$—, and —$CHOHCH_2CH_2$—. "$C_4$ linear hydroxyalkyl" refers to —$CH_2CH_2CH_2CHOH$—, —$CH_2CH_2CHOHCH_2$—, —$CH_2CHOHCH_2CH_2$—, and —$CHOHCH_2CH_2CH_2$—. Note that, for example, —$CH_2CHOHCH_2CH_2$— is understood to include both the fragment:

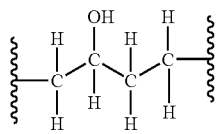

and the fragment:

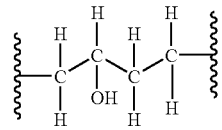

where the wavy lines indicate the attachment of the fragment to the remainder of the molecule; and similarly for the other hydroxyalkyl diradicals.

The term "alkenyl" refers to unsaturated aliphatic groups including straight-chain (linear), branched-chain, cyclic groups, and combinations thereof, having the number of carbon atoms specified, or if no number is specified, having up to 12 carbon atoms, which contain at least one double bond (—C=C—). Examples of alkenyl groups include, but are not limited to, —$CH_2$—CH=CH—$CH_3$; and —$CH_2$—$CH_2$-cyclohexenyl, where the ethyl group can be attached to the cyclohexenyl moiety at any available carbon valence. The term "alkynyl" refers to unsaturated aliphatic groups including straight-chain (linear), branched-chain, cyclic groups, and combinations thereof, having the number of carbon atoms specified, or if no number is specified, having up to 12 carbon atoms, which contain at least one triple bond (—C≡C—). "Hydrocarbon chain" or "hydrocarbyl" refers to any combination of straight-chain, branched-chain, or cyclic alkyl, alkenyl, or alkynyl groups, and any combination thereof. "Substituted alkenyl," "substituted alkynyl," and "substituted hydrocarbon chain" or "substituted hydrocarbyl" refer to the respective group substituted with one or more substituents, including, but not limited to, groups such as halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

"Aryl" or "Ar" refers to an aromatic carbocyclic group having a single ring (including, but not limited to, groups such as phenyl) or multiple condensed rings (including, but not limited to, groups such as naphthyl or anthryl), and includes both unsubstituted and substituted aryl groups. "Substituted aryls" refers to aryls substituted with one or more substituents, including, but not limited to, groups such as alkyl, alkenyl, alkynyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

"Heteroalkyl," "heteroalkenyl," and "heteroalkynyl" refer to alkyl, alkenyl, and alkynyl groups, respectively, that contain the number of carbon atoms specified (or if no number is specified, having up to 12 carbon atoms) which contain one or more heteroatoms as part of the main, branched, or cyclic chains in the group. Heteroatoms include, but are not limited to, N, S, O, and P; N and O are preferred. Heteroalkyl, heteroalkenyl, and heteroalkynyl groups may be attached to the remainder of the molecule either at a heteroatom (if a valence is available) or at a carbon atom. Examples of heteroalkyl groups include, but are not limited to, groups such as —O—$CH_3$, —$CH_2$—O—$CH_3$, —$CH_2$—$CH_2$—O—$CH_3$, —S—$CH_2$—$CH_2$—$CH_3$, —$CH_2$—CH($CH_3$)—S—$CH_3$, —$CH_2$—$CH_2$—NH—$CH_2$—$CH_2$—, 1-ethyl-6-propylpiperidino, 2-ethylthiophenyl, and morpholino. Examples of heteroalkenyl groups include, but are not limited to, groups such as —CH═CH—NH—CH(CH$_3$)—CH$_2$—. "Heteroaryl" or "HetAr" refers to an aromatic carbocyclic group having a single ring (including, but not limited to, examples such as pyridyl, thiophene, or furyl) or multiple condensed rings (including, but not limited to, examples such as imidazolyl, indolizinyl or benzothienyl) and having at least one hetero atom, including, but not limited to, heteroatoms such as N, O, P, or S, within the ring. Unless otherwise specified, heteroalkyl, heteroalkenyl, heteroalkynyl, and heteroaryl groups have between one and five heteroatoms and between one and twenty carbon atoms. "Substituted heteroalkyl," "substituted heteroalkenyl," "substituted heteroalkynyl," and "substituted heteroaryl" groups refer to heteroalkyl, heteroalkenyl, heteroalkynyl, and heteroaryl groups substituted with one or more substituents, including, but not limited to, groups such as alkyl, alkenyl, alkynyl, benzyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of such substituted heteroalkyl groups include, but are not limited to, piperazine, substituted at a nitrogen or carbon by a phenyl or benzyl group, and attached to the remainder of the molecule by any available valence on a carbon or nitrogen, —NH—SO$_2$-phenyl, —NH—(C═O)O-alkyl, —NH—(C═O)O-alkyl-aryl, and —NH—(C═O)-alkyl. If chemically possible, the heteroatom(s) as well as the carbon atoms of the group can be substituted. The heteroatom(s) can also be in oxidized form, if chemically possible.

The term "alkylaryl" refers to an alkyl group having the number of carbon atoms designated, appended to one, two, or three aryl groups.

The term "alkoxy" as used herein refers to an alkyl, alkenyl, alkynyl, or hydrocarbon chain linked to an oxygen atom and having the number of carbon atoms specified, or if no number is specified, having up to 12 carbon atoms. Examples of alkoxy groups include, but are not limited to, groups such as methoxy, ethoxy, and t-butoxy.

The term "alkanoate" as used herein refers to an ionized carboxylic acid group, such as acetate (CH$_3$C(═O)—O$^{(-1)}$), propionate (CH$_3$CH$_2$C(═O)—O$^{(-1)}$), and the like. "Alkyl alkanoate" refers to a carboxylic acid esterified with an alkoxy group, such as ethyl acetate (CH$_3$C(═O)—O—CH$_2$CH$_3$). "ω-haloalkyl alkanoate" refers to an alkyl alkanoate bearing a halogen atom on the alkanoate carbon atom furthest from the carboxyl group; thus, ethyl ω-bromo propionate refers to ethyl 3-bromopropionate, methyl ω-chloro n-butanoate refers to methyl 4-chloro n-butanoate, etc.

The terms "halo" and "halogen" as used herein refer to Cl, Br, F or I substituents.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis,* 2nd Ed. (John Wiley & Sons, Inc., New York). Amino protecting groups include, but are not limited to, mesitylenesulfonyl (Mes), benzyloxycarbonyl (CBz or Z), t-butyloxycarbonyl (Boc), t-butyldimethylsilyl (TBDIMS or TBDMS), 9-fluorenylmethyloxycarbonyl (Fmoc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5-bromo-7-nitroindolinyl, and the like. Hydroxylprotecting groups include, but are not limited to, t-butyl, benzyl, trityl, Fmoc, TBDIMS, photolabile protecting groups (such as nitroveratryl oxymethyl ether (Nvom)), Mom (methoxy methyl ether), and Mem (methoxy ethoxy methyl ether), NPEOC (4-nitrophenethyloxycarbonyl) and NPEOM (4-nitrophenethyloxymethyloxycarbonyl).

Synthetic Methods for Production of Oligoamine Compounds

Three general methods are presented herein for synthesizing the oligoamine compounds of the invention.

1. The first method involves repetitive addition of bromocyanoalkyl compounds to mesitylsulfonylated alkylamines as follows: the amino group of an alkylamine compound IA (such as methylamine, ethylamine, n-propylamine, n-butylamine, sec-butylamine, t-butylamine, and other alkylamine compounds, which are commercially available from Aldrich Chemical Company, Milwaukee, Wis., and other suppliers) is protected, e.g. by reaction with mesitylenesulfonyl chloride (available from Aldrich Chemical Company and other suppliers) to form a protected alkylamine IIA. The protected alkylamine IIA is treated with base, e.g. sodium hydride in anhydrous dimethylformamide, and then reacted with a haloalkylnitrile compound, such as 4-bromobutyronitrile or 3-bromopropionitrile (Aldrich). The nitrile moiety of the resulting product IIIA is reduced by various methods known in the art, such as treatment with hydrogen gas and palladium or platinum metal, to yield the free amine IVA. The forgoing steps—protection of the —NH$_2$ group (such as with the mesitylenesulfonyl group), and reaction of the —NH (Mes) moiety with a haloalkylnitrile followed by reduction with H$_2$ or other methods known in the art, is repeated until the desired number of nitrogen groups has been added. If a terminal alkyl group is desired, e.g. an ethyl group, it is added to the last nitrogen by simply reacting the last —NH(Mes) moiety with an alkyl halide (e.g., bromoethane, n-butyl chloride) instead of a haloalkylnitrile.

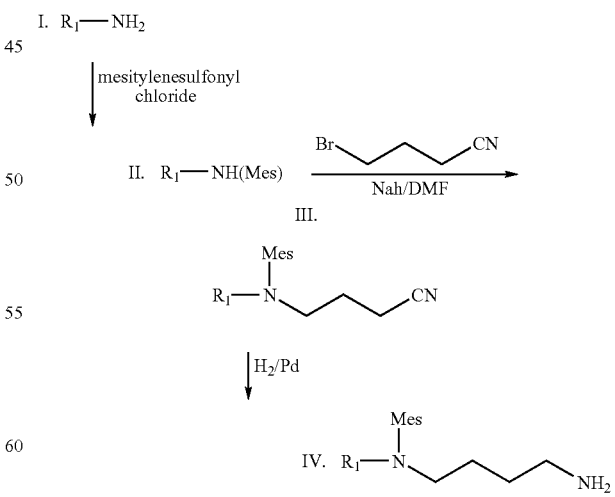

2. The second general method of preparing the saturated oligoamine compounds of the invention involves using chemistry analogous to that used for peptide synthesis to generate a polyamide chain, followed by reduction of the amide linkages to amines. A non-naturally occurring amino acid, such as $H_2NCH_2CH_2CH_2COOH$ or another compound where an amino group and carboxyl group are separated by a linear alkyl chain of one to twelve, one to eleven, one to eight, or one to seven $CH_2$ groups, can be converted into its N-protected derivative by using Boc, Fmoc, Cbz, or other amino protecting groups well-known in the art, as illustrated below by conversion of compound IB into compound IIB (PG indicates a protecting group).

In certain methods for synthesizing the compounds of the invention, the carboxyl group of the N-protected amino acid can then be converted into an amide group, which functions to prevent undesired reactions at the carboxyl group, and which will ultimately be converted into an amine group bearing the outermost alkyl groups of the final compound. That is, in certain methods for synthesizing the compounds of the invention, such as $CH_3CH_2(NHCH_2CH_2CH_2CH_2)_9NHCH_2CH_3$, converting the carboxyl group of Boc-$NHCH_2CH_2CH_2COOH$ into Boc-$NHCH_2CH_2CH_2CONHCH_2CH_3$ ultimately provides the ethyl groups flanking the repeating core of the molecule. This is shown for the general case for compound IIIB below. It should be noted that the designation "alkyl" in the scheme below can refer to groups which are identical or different, that is, alkyl can be used to designate both the —$CH_2CH_2CH_2$— group and a —$CH_2CH_3$ group as in Boc-$NHCH_2CH_2CH_2CONHCH_2CH_3$.

Once the carboxyl group of the N-protected amino acid is converted into an amide group, the N-terminus can be deprotected (compound IVB below). Another N-protected amino acid (which can be, but is not necessarily, identical to the amino acid used in the previous step), can then be added. The step is repeated until a desired length is reached, as in compound VB below.

IB.

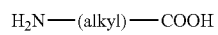

IIB.

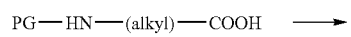

IIIB.

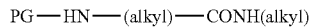

IVB.

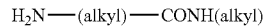

VB.

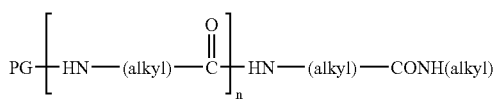

Once compound VB has been generated, it can be used in various further methods to synthesize the compounds of the invention. One such method is to reduce the amide groups of compound VB by various methods known in the art, using reagents such as borane (e.g., borane-tetrahydrofuran complex) or lithium aluminum hydride, to the compound VIB1 as follows.

VIB1.

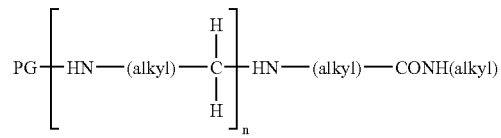

Two units of the reduced, appropriately protected compound VIIB1 (note that the protecting group designated "PG" can be the same or different from the protecting groups used in previous syntheses) are then condensed with a central alkyl group VIIIB1 (where "LG" designates a leaving group, which is displaced by the secondary nitrogen of VIIV1).

VIIB1.

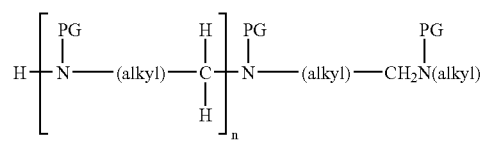

LG-(alkyl)-LG    VIIIB1.

While "alkyl" is used to designate the groups in the intermediates of the synthesis, unsaturated segments (alkenyl, alkynyl) groups can be used as well, provided that they are reduced at the end of the synthesis to alkyl groups.

Alternatively, if the desired number of alkyl links and nitrogens are present in intermediate VB, the compound can be acylated as depicted in VIB2:

VIB2.

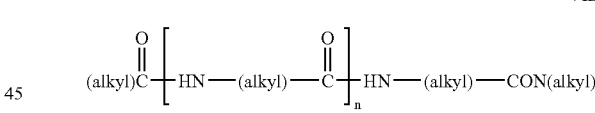

followed by reduction of the amides to amino groups. Amides can be reduced to amino groups using various methods known in the art, using reagents such as borane (e.g., borane-tetrahydrofuran complex) or lithium aluminum hydride. (Amine compound VIB1 can also be acylated and reduced to form the final compound, with appropriate protecting groups to prevent acylation of the secondary amines.)

While the synthetic scheme described above is performed in solution phase, solid-phase organic synthesis can also be employed. Since many of the reactions above are similar to reactions performed during solid-phase peptide synthesis, the reaction scheme above is readily adapted to solid-phase synthesis using techniques for peptide synthesis well-known in the art, as described in, for example, Atherton and Sheppard, *Solid Phase Peptide Synthesis: A Practical Approach*, New York: IRL Press, 1989; Stewart and Young: *Solid-Phase Peptide Synthesis* 2nd Ed., Rockford, Ill.: Pierce Chemical Co., 1984; and Jones, *The Chemical Synthesis of Peptides*, Oxford: Clarendon Press, 1994. Automated synthesis of the polyamides can be performed using an automated polypeptide synthesizer employing the solid phase method, such as those sold by Perkin Elmer-Applied Biosystems, Foster City, Calif. Following completion of the entire polyamide precursor, the polyamide is cleaved from the solid support and the amide groups are reduced to amine groups as described above.

3. The third general method of preparing the saturated oligoamine compounds of the invention comprises reduction of unsaturated polyamine compounds. Polyamine compounds which are conformationally restricted due to the presence of one or more double or triple bonds, such as those described in U.S. Pat. No. 5,889,061, WO 00/66587, and WO 98/17624, are reduced under a hydrogen atmosphere in the presence of finely divided platinum, palladium, nickel, or other hydrogenation catalysts well-known in the art (e.g., platinum dioxide or "Adam's catalyst;" platinum black; palladium on charcoal, Pd/C; Raney nickel).

Synthetic Methods for Production of Hydroxyoligoamine Compounds

Hydroxy groups can be readily incorporated into one or more locations of the oligoamine compounds. Example 11 below indicates a synthetic scheme for preparing an oligoamine with hydroxyl groups in two alkyl segments of the oligoamine. The method can be readily adapted to prepare oligoamines with hydroxy groups at any location in any segment of the molecule, simply by using the appropriate protected hydroxy amino acid. For example, $ZHN(CH_2)(CHOR)(CH_2)COOH$ can be used in place of $ZHN(CH_2)(CH_2)(CH_2)COOH$ for one of the segments of the oligoamine in any of the preceding general schemes, or in the schemes in the examples. This compound is readily synthesized from commercially available 4-amino-3-hydroxybutyric acid, by protecting the amino group with the Z group and then protecting the hydroxy group. The protecting group R on the hydroxy group can be TBDMS or any other hydroxy protecting group stable to the subsequent reaction conditions. As an additional example, $ZHN(CH_2)(CH_2)(CHOR)COOH$ (readily synthesized from commercially available 4-amino-2-hydroxybutyric acid) can be used to place the hydroxy group in an alternate location. The hydroxy-containing aminobutyric acids are available in enantiomerically pure R and S forms should stereospecific synthesis be desired.

Therapeutic Use of Oligoamine Compounds

Oligoamine compounds of the present invention are useful for treatment of a variety of diseases caused by uncontrolled proliferation of cells, including cancer, particularly prostate cancer, breast cancer, and other cancers. The oligoamine compounds of the present invention are also useful for treatment of infectious and microbial diseases, which can be caused by microorganisms, including, but not limited to, microorganisms such as bacteria, viruses, and parasites. In particular, the oligoamine compounds of the present invention are useful in treating diseases in immunocompromised patients. The oligoamine compounds of the present invention are particularly useful for treating microsporidiosis. (See Bacchi CJ et al., "Novel synthetic polyamines are effective in the treatment of experimental microsporidiosis, an opportunistic AIDS-associated infection," Antimicrob. Agents Chemother. 46(1):55-61 (2002); and Bacchi CJ et al., "SL-11158, a synthetic oligoamine, inhibits polyamine metabolism of *Encephalitozoon cuniculi*," J. Eukaryot. Microbiol. Suppl:92S-94S (2001)). The compounds are used to treat mammals, preferably humans. "Treating" a disease using an oligoamine compound of the invention is defined as administering one or more oligoamine compounds of the invention, with or without additional therapeutic agents, in order to prevent, reduce, or eliminate either the disease or the symptoms of the disease, or to retard the progression of the disease or of symptoms of the disease. "Therapeutic use" of the oligoamine compounds of the invention is defined as using one or more oligoamine compounds of the invention to treat a disease, as defined above. A "therapeutic amount" of the oligoamine compounds of the invention is an amount sufficient to treat a disease, as defined above.

In order to evaluate the efficacy of a particular oligoamine compound for a particular medicinal application, the compounds can be first tested against appropriately chosen test cells in vitro. In a non-limiting example, oligoamine compounds can be tested against tumor cells, for example, prostate tumor cells. Exemplary experiments can utilize cell lines capable of growing in culture as well as in vivo in athymic nude mice, such as LNCaP. Horoszewicz et al. (1983) *Cancer Res.* 43:1809-1818. Culturing and treatment of carcinoma cell lines, cell cycle and cell death determinations based on flow cytometry; enzyme assays including ODC, SAMDC and SSAT activities; and high pressure liquid chromatography detection and quantitation of natural polyamines and polyamine analogs are described in the art, for example, Mi et al. (1998) *Prostate* 34:51-60; Kramer et al. (1997) *Cancer Res.* 57:5521-27; and Kramer et al. (1995) *J. Biol. Chem.* 270:2124-2132. Evaluations can also be made of the effects of the oligoamine compound on cell growth and metabolism.

Analysis begins with $IC_{50}$ determinations based on dose-response curves ranging from 0.1 to 1000 µM performed at 72 hr. From these studies, conditions can be defined which produce about 50% growth inhibition and used to: (a) follow time-dependence of growth inhibition for up to 6 days, with particular attention to decreases in cell number, which may indicate drug-induced cell death; (b) characterize oligoamine compound effects on cell cycle progression and cell death using flow cytometry (analysis to be performed on attached and detached cells); (c) examine oligoamine compound effects on cellular metabolic parameters. Oligoamine compound effects can be normalized to intracellular concentrations (by HPLC analysis), which also provide an indication of their relative ability to penetrate cells. Marked differences in oligoamine compound uptake can be further characterized by studying the compound's ability to utilize and regulate the polyamine transporter, as assessed by competition studies using radiolabeled spermidine, as previously described in Mi et al. (1998). Oligoamine compounds could also enter the cells by a diffusion mechanism.

In Vivo Testing of Oligoamine Compounds

Oligoamine compounds found to have potent anti-proliferative activity in vitro towards cultured carcinoma cells can be evaluated in in vivo model systems. In a non-limiting protocol, the first goal is to determine the relative toxicity of the compounds in non-tumor-bearing animals, such as DBA/2 mice. Groups of three animals each can be injected intraperitoneally with increasing concentrations of an oligoamine compound, beginning at, for example, 10 mg/kg. Toxicity as indicated by morbidity is closely monitored over the first 24 hr. A well-characterized polyamine analog compound, such as BE-333, can be used as an internal standard in these studies, since a data base has already been established regarding acute toxicity via a single dose treatment relative to chronic toxicity via a daily×5 d schedule. Thus, in the case of oligoamine compounds, single dose toxicity relative to BE-333 is used to project the range of doses to be used on a daily×5 d schedule.

After the highest tolerated dosage on a daily×5 d schedule is deduced, antitumor activity is determined. Typically, tumors can be subcutaneously implanted into nude athymic mice by trocar and allowed to reach 100-200 $mm^3$ before initiating treatment by intraperitoneal injection daily×5 d. Most oligoamine compounds can be given in a range between 10 and 200 mg/kg. Oligoamine compounds can be evaluated at three treatment dosages with 10-15 animals per group (a minimum of three from each can be used for pharmacodynamic studies, described below). Mice can be monitored and weighed twice weekly to determine tumor size and toxicity. Tumor size is determined by multi-directional measurement from which volume in $mm^3$ is calculated. Tumors can be followed until median tumor volume of each group reaches 1500 $mm^3$ (i.e., 20% of body weight), at which time the animals can be sacrificed. Although the initial anti-tumor studies focuses on a daily×5 d schedule, constant infusion can be performed via Alzet pump delivery for 5 days since this schedule dramatically improves the anti-tumor activity of BE-333 against A549 human large cell hung carcinoma. Sharma et al. (1997) *Clin. Cancer Res.* 3:1239-1244. In addition to assessing anti-tumor activity, free oligoamine compound levels in tumor and normal tissues can be determined in test animals.

Methods of Administration of Oligoamine Compounds

The oligoamine compounds of the present invention can be administered to a mammalian, preferably human, subject via any route known in the art, including, but not limited to, those disclosed herein. Methods of administration include but are not limited to, intravenous, oral, intraarterial, intratumoral, intramuscular, topical, inhalation, subcutaneous, intraperitoneal, gastrointestinal, and directly to a specific or affected organ. The oligoamine compounds described herein are administratable in the form of tablets, pills, powder mixtures, capsules, granules, injectables, creams, solutions, suppositories, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

The pharmaceutical dosage form which contains the compounds described herein is conveniently admixed with a non-toxic pharmaceutical organic carrier or a non-toxic pharmaceutical inorganic carrier. Typical pharmaceutically-acceptable carriers include, for example, mannitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical dosage form can also contain non-toxic auxiliary substances such as emulsifying, preserving, or wetting agents, and the like. A suitable carrier is one which does not cause an intolerable side effect, but which allows the novel oligoamine compound(s) to retain its pharmacological activity in the body. Formulations for parenteral and nonparenteral drug delivery are known in the art and are set forth in *Remington's Pharmaceutical Sciences*, 18th Edition, Mack Publishing (1990) and *Remington, The Science and Practice of Pharmacy*, Lippincott Williams & Wilkins (2000). Solid forms, such as tablets, capsules and powders, can be fabricated using conventional tableting and capsule-filling machinery, which is well known in the art. Solid dosage forms, including tablets and capsules for oral administration in unit dose presentation form, can contain any number of additional non-active ingredients known to the art, including such conventional additives as excipients; desiccants; colorants; binding agents, for example syrup, acacia, gelatin, sorbitol, tragacanth, or polyvinylpyrollidone; fillers, for example lactose, sugar, maize-starch, calcium phosphate, sorbitol or glycine; tableting lubricants, for example magnesium stearate, talc, polyethylene glycol or silica; disintegrants, for example potato starch; or acceptable wetting agents such as sodium lauryl sulfate. The tablets can be coated according to methods well known in standard pharmaceutical practice. Liquid forms for ingestion can be formulated using known liquid carriers, including aqueous and non-aqueous carriers, suspensions, oil-in-water and/or water-in-oil emulsions, and the like. Liquid formulations can also contain any number of additional non-active ingredients, including colorants, fragrance, flavorings, viscosity modifiers, preservatives, stabilizers, and the like. For parenteral administration, oligoamine compounds can be administered as injectable dosages of a solution or suspension of the compound in a physiologically acceptable diluent or sterile liquid carrier such as water or oil, with or without additional surfactants or adjuvants. An illustrative list of carrier oils would include animal and vegetable oils (e.g., peanut oil, soy bean oil), petroleum-derived oils (e.g., mineral oil), and synthetic oils. In general, for injectable unit doses, water, saline, aqueous dextrose and related sugar solutions, and ethanol and glycol solutions such as propylene glycol or polyethylene glycol are preferred liquid carriers. The pharmaceutical unit dosage chosen is preferably fabricated and administered to provide a final concentration of drug at the point of contact with the cancer cell of from 1 μM to 10 mM. More preferred is a concentration of from 1 to 100 μM. The optimal effective concentration of oligoamine compounds can be determined empirically and will depend on the type and severity of the disease, route of administration, disease progression and health and mass or body area of the patient. Such determinations are within the skill of one in the art. Oligoamine compounds can be administered as the sole active ingredient, or can be administered in combination with another active ingredient, including, but not limited to, cytotoxic agents, antibiotics, antimetabolites, nitrosourea, vinca alkaloids, polypeptides, antibodies, cytokines, etc.

EXAMPLES

Chemical Synthesis Examples

The following examples are illustrative of the manufacture of several compounds according to the present invention, and are not intended to limit the invention disclosed and claimed herein in any fashion. The Examples are included herein solely to aid in a more complete understanding of the present invention.

All commercially available reagents were used without further purification. All reactions were followed by TLC (silica gel $F_{264}$ precoated, Merck); column chromatography was carried out with silica gel (Merck 60, 0.040-0.063 mesh). The detection was performed either with UV light or the following reagents: $KMnO_4$ soln. (1:1 mixture of 1% aq. $KMnO_4$ soln. and 5% aq. $Na_2CO_3$ soln.); Schlittler reagent (iodine platinate) (1 g $H_2PtCl_6$ in 6 ml $H_2O$, 20 ml 1N HCl and 25.5 g KI in 225 ml $H_2O$ diluted to 1 L) for amides and amines. IR measurements are presented in units of $[cm^{-1}]$ and were recorded on a Perkin-Elmer 781 instrument. NMR spectra were recorded on Bruker-300 or Bruker AMX-600 instruments with δ in ppm and using the appropriate solvent as internal standard. MS spectra were generated on Finnigan MAT SSO 700 or Finnigan MAT 90 instruments using chemical ionization (CI) with $NH_3$ and electron impact (EI; 70 eV), and on a Finnigan TSQ 700 instrument using electrospray ionization (ESI).

Example 1

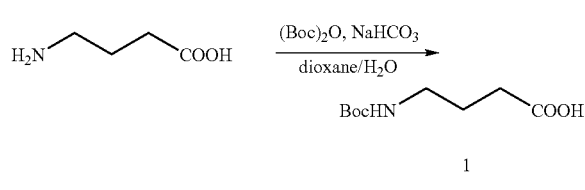

N-Boc-γ-Aminobutyric acid (1): (This compound can also be purchased commercially from Sigma-Aldrich Chemical Company, Saint Louis, Mo., USA, product B 1892). A solution of $Boc_2O$ (95 g, 435 mmol) in 600 ml of dioxane was added at 0° C. to a stirred mixture of $NaHCO_3$ (73 g, 870 mmol) in $H_2O$ (500 ml) and γ-aminobutyric acid (30 g, 291 mmol), stirred for 1 h at 0° C. and for 10 h at 20° C. The reaction mixture was diluted with $H_2O$ (500 ml), extracted 3 times with $CHCl_3$, the aqueous layer was acidified with 3% HCl to pH 7 and then with $KHSO_4$ (20% aq. solution) to pH 2. The product was extracted 5 times with $CHCl_3$, dried ($Na_2SO_4$) concentrated in vacuo, and crystallized from $Et_2O$-petr. ether. Yield 54.05 g (97%). mp: 58-59° C. NMR ($CDCl_3$): 1.44 (s, 9H), 1.83 (m, 2H), 2.40 (t, J=7.15, 2H), 3.10-3.30 (m, 2H), 4.7 (bs, 1H).

Example 2

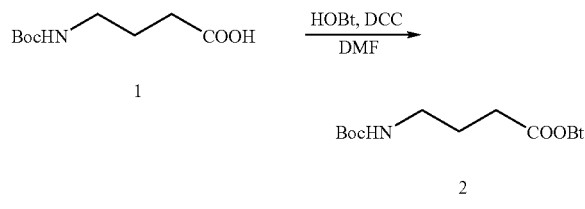

1-Hydroxybenzotriazole derivative of N-Boc-γ-Aminobutyric acid (2): 1-Hydroxybenzotriazole (70.3 g, 520 mmol; abbreviated as "HOBt" as individual reagent and as "Bt" indicating ester) and dicyclohexylcarbodiimide (DCC, 107.41 g. 520 mmol) were added into an ice cold solution of the acid 1 (105.5 g, 519 mmol) in DMF (700 ml), the cooling bath was removed and the reaction mixture was stirred overnight at 20° C. DMF was evaporated in vacuo at 40° C., the residue was suspended in $CH_2Cl_2/H_2O$ (2:1) mixture (1.5 liter), filtered, and the precipitate was washed with $CH_2Cl_2$ The washings and filtrate were combined, washed 4 times with $H_2O$, washed with brine, dried ($Na_2SO_4$) and concentrated in vacuo. The product was re-precipitated from hot $CH_2Cl_2$ with $Et_2O$. The mother liquor was concentrated and the residue was re-precipitated again from hot $CH_2Cl_2$ with $Et_2O$. Both crops were combined, dried in vacuo to obtain 151 g (87% of 2 as a mixture of N- and O-isomers, which was used in the following steps without further purification. mp: 52-55° C. $^1H$ NMR ($CDCl_3$): 1.41 (s) 1.47 (s), 1.98-2.10 (m), 2.87 (t, J=7.16), 3.18 (t, J=7.15), 3.27-3.36 (m), 4.71 (bs), 7.42-7.44 (m), 7.47-7.60 (m), 7.76-7.79 (m), 7.99-8.04 (m), 8.05-8.08 (m), 8.39-8.43 (m). ESI-MS: 663.2 ($M_2Na^+$), 641.4 ($M_2H^+$), 456.2, 342.0 ($MNa^+$), 321.2 ($MH^+$).

Example 3

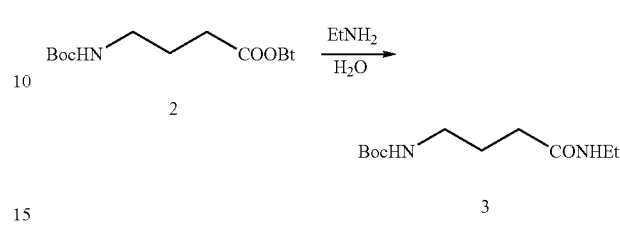

(3-Ethylcarbamoyl-propyl)-carbamic acid tert-butyl ester (3): An aqueous solution of ethylamine (70%, 41 ml) was added into an ice cold solution of benzotriazole derivative 2 (50 g, 156 mmol) in $CH_2Cl_2$ (500 ml), stirred for 1 h at room temperature, diluted 2 times with $CH_2Cl_2$, washed with $H_2O$, then brine, dried ($Na_2SO_4$), concentrated and dried in vacuo. Yield 32.845 g (91%). mp: 82-83° C. $^1H$ NMR ($CDCl_3$): 1.15 (t, J=7.27, 3H), 1.44 (s, 9H), 1.75-1.85 (m, 2H), 2.20 (t, J=7.10, 2H), 3.17 (q, J=6.49, 2H), 3.24-3.34 (m, 2H), 4.82 (s, 1H), 6.13 (bs, 1H). $^{13}C$ NMR ($CDCl_3$): 14.72, 24.91, 26.33, 28.35, 33.66, 33.92, 34.32, 39.78, 79.21, 156.44, 172.43. ESI-MS: 483.4 ($M_2Na^+$), 461.4 ($M_2H^+$), 321.2 ($MH^+$).

Example 4

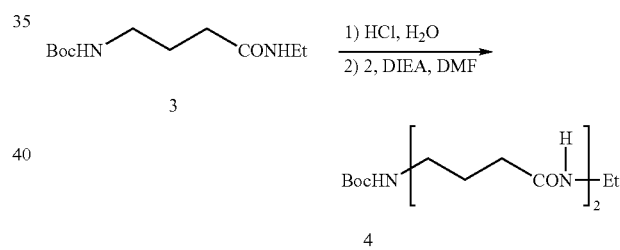

[3-(3-Ethylcarbamoyl-propylcarbamoyl)-propyl]-carbamic acid tert-butyl ester 4. Hydrochloric acid (12%, 64 ml) was added to a cold solution of Boc-derivative 3 (21.1 g, 91.7 mmol) in MeOH (190 ml) and stirred overnight at room temperature. The next day additional acid (30 ml) was added and stirring was continued for another 10 h. The reaction mixture was filtered, washed with $CHCl_3$, concentrated and dried in vacuo overnight. The product was suspended in DMF (300 ml) with DIEA (42 ml), cooled to 0° C. and a solution of Bt-derivative 2 (29 g, 90.5 mmol) in DMF (100 ml) was added into the reaction mixture. The cooling bath was removed and the stirring was continued overnight. The solvent and DIEA were removed in vacuo at 45° C., the residue was suspended in $CHCl_3/H_2O$ mixture, washed with $H_2O$, aq. $KHSO_4$ (20%), $H_2O$, aq. $NaHCO_3$ (2 times with each), dried ($Na_2SO_4$), concentrated in vacuo, and triturated with petr. ether. Yield 22.32 g (78%). mp: 134-1350. $^1H$ ($CDCl_3$): 1.15 (t, J=7.27, 3H), 1.44 (s, 9H), 1.65-1.95 (m, 4H), 2.20-2.26 (m, 4H), 3.19 (q, J=6.15, 2H), 3.23-3.35 (m, 4H), 4.82 (bs, 1H), 6.40 (bs, 1H), 6.68 (bs, 1H). $^{13}C$ ($CDCl_3$): 14.77, 24.92, 25.66, 26.43, 28.38, 33.59, 33.84, 33.92, 34.35, 38.83, 39.66, 79.35, 156.56, 172.65, 173.12. ESI-MS: 338.2 (MNa⁺), 316.0 (MH⁺), 216.0 (MH⁺-Boc).

Example 5

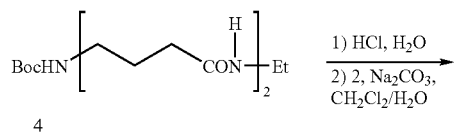

{3-[3-(3-Ethylcarbamoyl-propylcarbamoyl)-propylcarbamoyl]-propyl}-carbamic acid tert-butyl ester 5. Boc-Protected derivative 4 (22.3 g, 70.7 mmol) was stirred in a mixture of MeOH (200 ml) and HCl (12%, 81 ml) for 48 h, concentrated to dryness in vacuo, dissolved in H₂O, and washed 3 times with CHCl₃. Water was removed on a rotary evaporator at 45° C. The resulting hydrochloride was dissolved in a mixture of CH₂Cl₂ (600 ml) and aq. Na₂CO₃ (20%, 100 ml), cooled on an ice bath, and Bt-derivative 2 (22.47 g, 70.15 mmol) was added. The cooling bath was removed and the mixture was stirred for 18 h with a mechanical stirrer. The main part of the CH₂Cl₂ was removed on a rotary evaporator, the reaction mixture was suspended in water and filtered. The product was triturated in EtOAc, filtered, washed with petr. ether and dried in vacuo. Yield 25.46 g (90%). mp: 170-171° C. ¹H NMR (CDCl₃/CD₃OD): 1.14 (t, J=7.30, 3H), 1.44 (s, 9H), 1.72-1.85 (m, 6H), 2.10-2.23 (m, 6H), 3.06-3.12 (m, 2H), 3.18-3.26 (m, 6H), 5.57 (bs, 1H), 7.32 (bs, 1H), 7.46 (bs, 1H), 7.60 (bs, 1H). ¹³C NMR (CDCl₃/CD₃OD): 14.22, 24.73, 25.32, 25.39, 25.96, 28.15, 33.33, 33.59, 34.12, 34.25, 38.60, 39.64, 79.29, 156.68, 173.39, 173.88. ESI-MS: 423.4 (MNa⁺), 401.4 (MH⁺).

Example 6

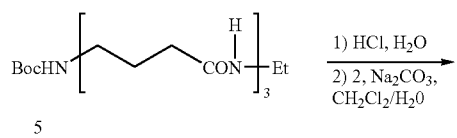

{3-{3-[3-(3-Ethylcarbamoyl-propylcarbamoyl)-propylcarbamoyl]-propylcarbamoyl}-propyl}-carbamic acid tert-butyl ester 6 was prepared from Boc derivative 5 (25.175 g) employing the same procedure as for 5 with the yield 24.79 g, (81%). mp: 196-197° C. ¹H NMR (CDCl₃/CD₃OD): 1.14 (t, J=7.28, 3H), 1.44 (s, 9H), 1.74-1.85 (m, 8H), 2.15-2.24 (m, 8H), 3.10 (q, J=6.22, 2H), 3.18-3.26 (m, 8H), 5.55 (bs, 1H), 7.28 (bs, 1H), 7.43 (bs, 1H), 7.55 (bs, 1H), 7.62 (bs, 1H). ¹³C NMR (CDCl₃/CD₃OD): 13.88, 24.56, 25.14, 25.23, 25.75, 27.90, 33.07, 33.37, 33.94, 38.34, 39.35, 79.04, 156.67, 173.37, 173.76, 173.86. ESI-MS: 508.4 (MNa⁺), 486.4 (MH⁺).

Example 7

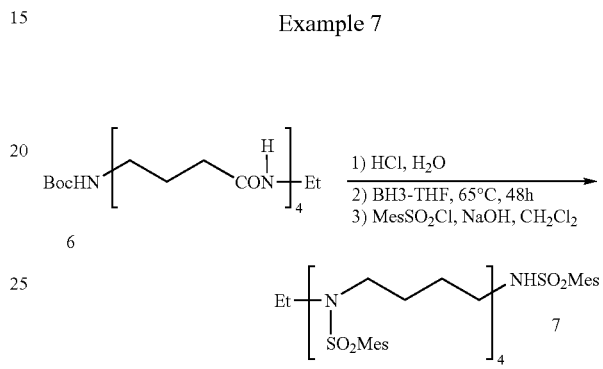

¹N,⁶N,¹¹N,¹⁶N,²¹N-Pentakis(mesitylenesulfonyl)-1,6,11,16,21-pentazatricosane 7. Boc derivative 6 (24.80 g, 51.06 mmol) was dissolved in a cold MeOH (370 ml)/aq. HCl (12%, 150 ml) solution, stirred for 48 h at room temperature, concentrated on a rotary evaporator at 45° C., dissolved in a minimum of H₂O, washed 2 times with CHCl₃, transferred into a 2 L round-bottom flask, and dried in vacuo. The product was stirred with BH₃-THF (1 M, 1 L) at 65° C. for 24 h, 200 ml more of BH₃-THF solution was added, and the reaction was continued for another 72 h. The reaction mixture was cooled to 0° C., quenched with HBr (30% in AcOH) until evolution of H₂ stops (approx. 300 ml), half of the solvent was removed on a rotary evaporator (5 mm, 55° C.), more HBr/AcOH (500 ml) was added, and left overnight. The reaction mixture was concentrated again on a rotary evaporator (5 mm, 55° C.) until it became very viscous, and triturated with a mixture HCl (6%, 1 L) and CHCl₃ (200 ml), and filtered. The CHCl₃ layer was extracted 3 times with H₂O, the aqueous phases were combined, washed again with CHCl₃, and concentrated to dryness on a rotary evaporator at 55° C.

The residue was suspended in a mixture of CH₂Cl₂ (400 ml) and NaOH (2N, 560 ml), cooled on an ice bath, and sulfonyl chloride (61.2 g, 280 mmol) in CH₂Cl₂ (400 ml) was added in a few portions into the stirred reaction mixture. The cooling bath was removed and the stirring was continued for 10 h. The reaction mixture was diluted twice with CHCl₃, mixed with 200 ml of H₂O, filtered, and the precipitate was washed with CHCl₃ and H₂O. The filtrate and washings were combined, washed 4 times with H₂O, brine, dried (Na₂SO₄), concentrated and purified on a column (SiO₂, EtOAc:hexane=1:1). Yield 36.8 g (77%). mp: 58-60° C. ¹HNMR (CDCl₃): 0.96 (t, J=7.14, 3H), 1.23-1.40 (m, 16H), 2.29 (s, 15H), 2.54, 2.56, 2.58 (s, together 30H), 4.55 (t, J=6.30, 1H), 6.93 (s, 10H).

MALDI-MS: 1278.618 (MK+), 1262.600 (MNa+), 1240.712 (M+).

Example 8

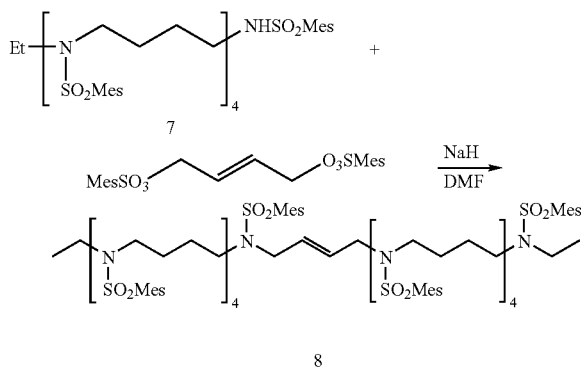

$^3$N,$^8$N,$^{13}$N,$^{18}$N$^{23}$N,$^{28}$N$^{33}$N,$^{38}$N,$^{43}$N,$^{48}$N-Decakis(mesitylenesulfonyl)-3,8,13,18,23,28,33,38,43,48-decaazapentacontene-25 (8). Sodium hydride (60% suspension in oil, 712 mg, 17.8 mmol) was added to an ice cold stirred solution of the product 6 (18.4 g, 14.83 mmol) in DMF (185 ml), stirred for 10 min and 2-butene-1,4-diyl bis[mesitylenesulfonate] (3.356 g, 7.42 mmol) was added into the reaction mixture. The stirring was continued for 3 h at 0° C. and left overnight. After the mixture was cooled to 0° C., it was quenched with ice water, concentrated in vacuo at 50° C., dissolved in CHCl$_3$, washed 4 times with aq. NH$_4$Cl, dried (Na$_2$SO$_4$), filtered and concentrated on a rotary evaporator. Yield: 16.9 g (90%). The product was utilized in the following steps without further purification.

mp: 73-74° C. $^1$H NMR (CDCl$_3$): 0.96 (t, J=7.19, 6H), 7.15-7.40 (m, 32H), 2.29 (s, 30H), 2.52, 2.53, 2.54, 2.55 (s, 60H), 2.85-3.19 (m, 36H), 4.13 (d, J=3.93, 4H), 5.42 (bs, 2H), 6.92 (s, 20H). $^{13}$C NMR (CDCl$_3$): 12.70, 20.92, 22.76, 24.44, 24.61, 24.73, 40.02, 42.07, 44.53, 44.92, 45.59, 128.30, 131.95, 132.89, 133.35, 139.95, 140.09, 142.29, 142.59.

Example 9

3,8,13,18,23,28,33,38,43,48-Decaazapentacontane decahydrochloride 9. The product 8 (32.2 g 12.7 mmol) was dissolved in 500 ml of CH$_2$Cl$_2$, cooled to 0° C., and PhOH (119.7 g, 1.27 mol) followed by 510 ml of HBr (30% in AcOH) were added into the solution. The mixture was stirred for 15 h at 20° C., quenched with 1000 ml of ice water, and the organic layer was separated and extracted one time with 150 ml of H$_2$O. The aqueous phases were combined, washed with CH$_2$Cl$_2$ (8×150 ml), concentrated on a rotary evaporator at 50° C. to the volume of 600 ml, and stiffed overnight with 1 g of activated carbon. Following filtration through a CELITE cake (CELITE is a registered trademark for diatomaceous earth of the Celite Corporation) and rinsing the cake with H$_2$O, the filtrate was transferred into a Parr apparatus and subjected hydrogenation with 3 g of Pd on C (10%) for 48 h at 50 psi. The catalyst was removed by filtration through a CELITE cake and rinsed with H$_2$O; the H$_2$O was removed on a rotary evaporator at 50° C. The residue was dissolved in EtOH, cooled to 0° C. and product was precipitated with 35% HCl. Finally it was filtered, triturated with EtOH and dried in vacuo. Yield 11 g (80%). mp: above 210° C. $^1$H NMR (D$_2$O): 1.27 (t, J=7.37, 6H), 1.62-1.88 (m, 36H), 2.95-3.25 (m, 40H). $^{13}$C NMR (D$_2$O): 13.31, 25.59, 45.68, 49.04, 49.66. MALDI-MS: 850.2 (MH$^+$ HCl), 714.0 (MH$^+$), 515.2, 543.8, 357.8.

Example 10

1,4-Bis(mesitylenesulfonyloxy)butane (11) 1,4-Butanediol (4.5 g, 50 mmol) was dissolved in dioxane (30 ml), and a 50% solution of KOH (45 ml) and benzyl triethylammonium bromide (675 mg, 2.5 mmol) were added. The mixture was stirred and cooled at 5° C., and mesitylenesulfonyl chloride (26 g, 120 mmol) was added in small portions. The mixture was kept for 5 hr at 5° C., excess water was added and the mixture was stirred for 18 h at 25° C. The solid was filtered, dried and crystallized from ethyl acetate/hexane; 14.6 g (64%) of 11 were obtained; mp 108.6° C.; $^1$H-NMR (CDCl$_3$) δ 1.75 (t, 4H), 2.30 (s, 6H), 2.60 (s, 12H), 3.95 (t, 4H), 6.95 (s, 4H). $^{13}$CNMR (CDCl$_3$) δ 20.94, 22.48, 25.15, 68.30, 131.70, 139.72, 143.29. MS-MALDI (m/z) 477.2 (M$^+$+Na), 493.1 (M$^+$+K).

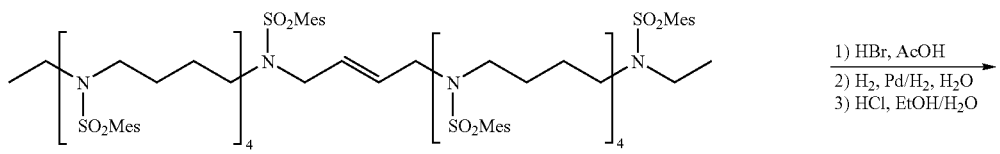

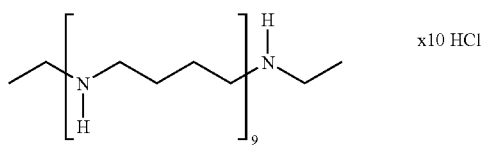

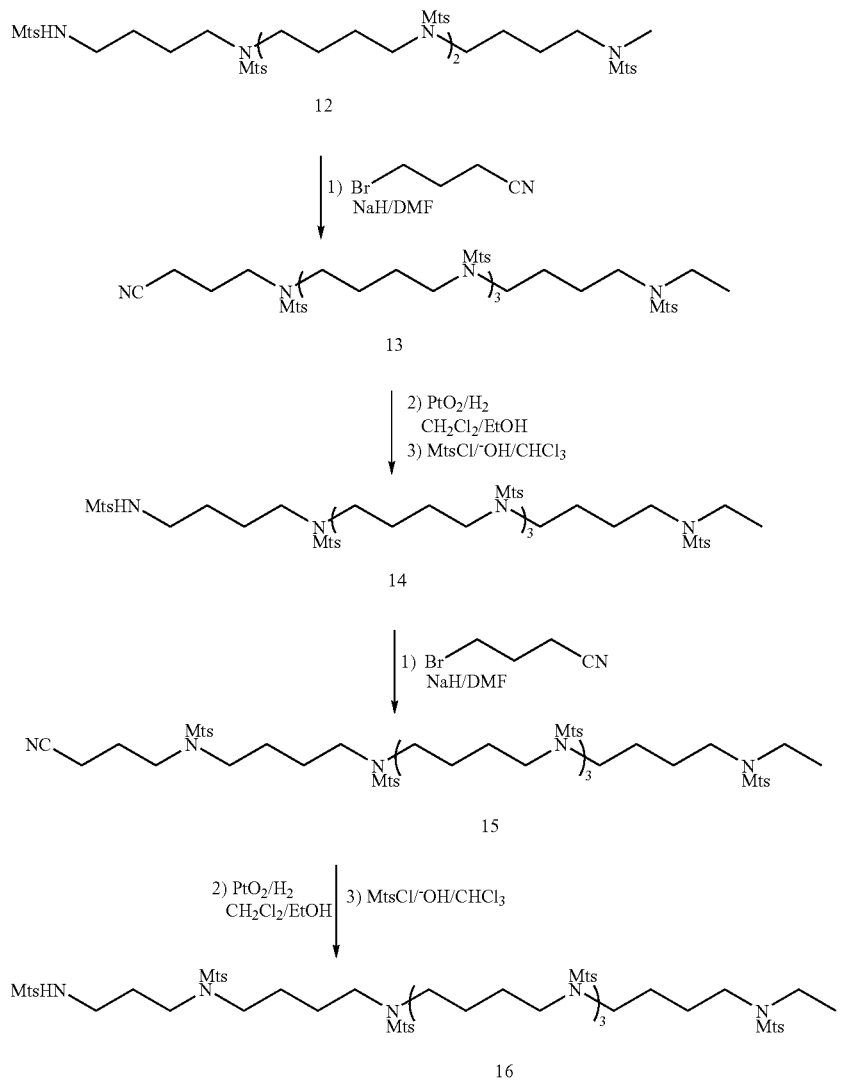

Compound 16. Amide 16 was prepared starting with pentamide 12 (described in International Patent Application WO 00/66587) following the sequence of reactions described in WO 00/66587, namely, alkylation with 4-bromobutyronitrile, followed by reduction of the nitrile 13 and protection with mesitylene chloride to give 14. Repeating the sequence of reactions gave compound 15, then compound 16.

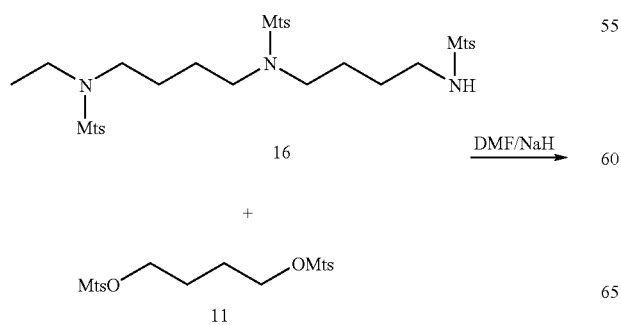

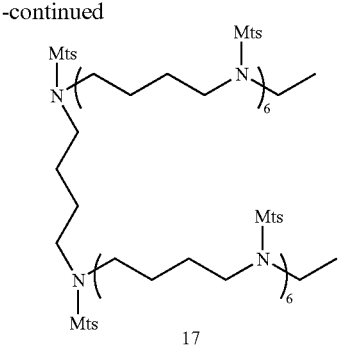

Compound 17. Amide 16 (350 mg, 0.2 mmol) was dissolved in DMF (10 ml), the solution stirred at 5° C. under $N_2$, and 60% NaH (10 mg) was added. Compound 11 was added, the mixture was allowed to reach 25° C. and was kept for 18 h. The solvent was evaporated and the residue was extracted with chloroform, the extracts were washed twice with saturated ammonium chloride, dried (Na$_2$SO$_4$) and evaporated. The residue was purified by filtration through a silica gel column using hexane/ethyl acetate (6:5) as eluant; 140 mg of 17 (39%) were obtained. $^1$H NMR (CDCl$_3$), δ 1.0 (t, 6H), 1.30 (m, 52H), 2.30 (s, 42H), 2.55 (s, 84H), 3.0 (m, 56H), 6.95 (s, 28H). $^{13}$C NMR δ 12.68, 20.89, 22.67, 22.74, 24.38, 24.46, 24.74, 40.03, 44.55, 44.85, 44.96, 131.86, 133.37, 139.95, 142.28.

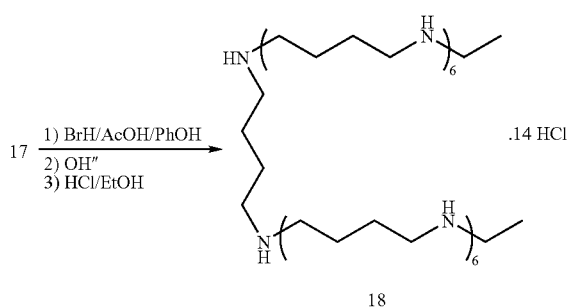

Compound 17 was deprotected to give tetradecamine 18 using HBr/AcOH as described in International Patent Application WO 00/66587 for compound 43 of that document, at pages 42-43.

Example 11

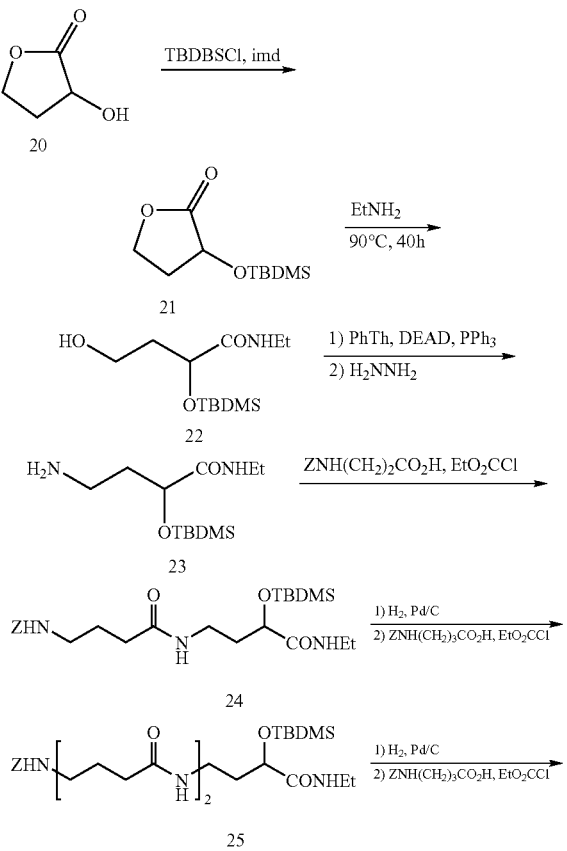

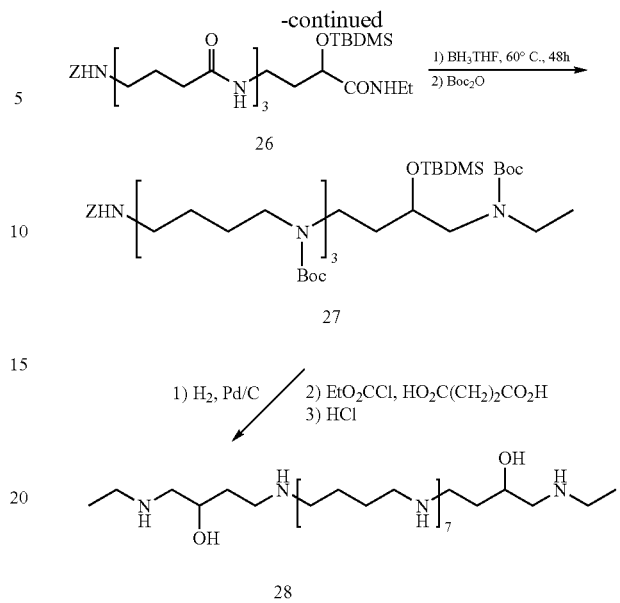

Preparation of 5,46-Dihydroxy-3,8,13,18,23,28,33,38,43,48-decaazapentacontane decahydrochloride 28. 2-Hydroxy-γ-butyrolactone 20 was used as a starting material. (This compound is commercially available as both R and S isomers.) Following the protection of hydroxy group with t-butyldimethylsilyl chloride (TBDMSCl), the resulting lactone 21 was treated with a THF solution of EtNH$_2$. The resulting hydroxy amide 22 was subjected to a Mitsunobu reaction with phthalimide (PhTh), diethylazodicarboxylate (DEAD), and triphenylphosphine, followed by deprotection with hydrazine to obtain amine 23. Amine 23 was repeatedly acylated with γ-carbobenzyloxy-aminobutyric acid in presence of ethyl chloroformate and the carbobenzyloxy (Z) group was removed by hydrogenation over Pd/C catalyst to yield products 24-26. Reduction of tetramide 26 with the borane-THF complex, followed by treatment of the resulting tetramine with Boc-anhydride, gave 27. This product was acylated with succinic acid after removal of the Z group by hydrogenation, then Boc-deprotected with aqueous HCl and the amide groups were again reduced using BH$_3$-THF reagent to yield desired product 28 as a decahydrochloride. The 5R, 46R and 5S, 46S analogues are prepared by using the R or S isomers of 2-hydroxy-γ-butyrolactone, respectively, as the starting material.

Example 12

Calf-thymus DNA aggregation by spermine and oligoamines. The oligoamines of the invention are very efficient in producing DNA aggregation. The concentrations required for polyamines at the start of DNA aggregation along with the concentration required for spermine to achieve the same can be seen in Table 1. The oligoamines aggregated DNA 20 to 40 times more efficiently than spermine under identical conditions.

Test for DNA Aggregation: DNA aggregation was studied using a Perkin-Elmer Lambda 25 UV/visible spectrophotometer connected to a PTP 6 heating unit using a previously published procedure (see Basu, H S and Marton, L J, "The interaction of spermine and pentamines with DNA," Biochemical Journal 244:243-246 (1987)). Aggregation was determined in 50 mM NaCl, 1 mM Na-cacodylate pH 7.0 buffer by observing the increase in DNA absorbance (approximately 0.5 $A_{260}$ units) at 320 nm.

TABLE 1

DNA Aggregation

| Polyamine | Conc. (µM) at the start of DNA Aggregation |
|---|---|
| Spermine | 88.5 |
| SL-11159 | 2.5 |
| SL-11160 | 4.5 |
| SL-11175 | 2.0 |
| SL-11226 | 2.2 |

Example 13

Effect of Saturated Oligoamines on Human Prostate Tumor Cell Growth by the MTT assay. Saturated oligoamines inhibited prostate cancer cell growth in vitro. DU-145 cells were most sensitive and PC-3 cells were less sensitive to the effects of oligoamines. In general, $ID_{50}$ values of less than 0.5 µM were obtained (Table 2). Even though the PC-3 cells were relatively more resistant to the oligoamines, at a 5 µM concentration the oligoamines reduced the cell number to less than 1% of the control on day 6 of incubation. Tissue cultures and the MTT assay were performed as follows.

Tissue Culture. Cells were seeded into 75 cm² culture flasks with 15 ml of Eagle's minimal essential medium supplemented with 10% fetal calf serum and nonessential amino acids. The flasks were incubated in a humidified 95% air/5% $CO_2$ atmosphere. The cells were grown for at least 24 h to ensure that they are in the log phase of growth and then they were treated with the oligoamines. Cells were harvested by treatment for 5 min with STV (saline A, 0.05% trypsin, 0.02% EDTA) at 37° C. The flasks were rapped on the lab bench, pipetted several times and aliquots of cell suspension were withdrawn and counted using a Coulter particle counter that has been standardized for counting each cell line using a hemacytometer.

MTT Assay: Trypsinized cell suspensions were diluted to seed 80 µl suspensions containing 500 cells in each well of a 96 well Corning microtiter plate and incubated overnight at 37° C. in a humidified incubator in 5% $CO_2$. 20 µl of appropriately diluted stock solution of each drug were added to the middle 8 columns of cell suspension in the microtiter plates. Each drug concentration was run in quadruplicate. Outer columns of the plates were used for buffer controls. Cells were incubated with the drug for 6 days at 37° C. in 5% $CO_2/H_2O$ atmosphere. 25 µl of 5 mg/ml solution of 3-(4,5-dimethylthiazol-2-yl)-2,5-diphenyl tetrazolium bromide (MTT) were added to each well and incubated for 4 hours at 37° C. in 5% $CO_2/H_2O$ incubator. Cells were lysed by incubating overnight with 100 µl lysis buffer (500 ml of the lysis buffer contains: 100 g lauryl sulfate (SDS), 250 ml of N,N-dimethylformamide, and 2 ml of glacial acetic acid, made up to volume with water; pH 4.8).

The color was monitored at room temperature at 570 nm in a E-max Precision Microplate Reader (Molecular Devices Corporation, Sunnyvale, Calif.) and data was analyzed using cell survival software supplied by Molecular Devices Corporation.

TABLE 2

| Oligo-amines | Structures of Oligoamines | $ID_{50}$ (µM) values for Human Tumor Cell Lines | | | |
|---|---|---|---|---|---|
| | | LnCap | DU145 | DuPro | PC-3 |
| SL-11159 | (structure) .10 HCl | 0.25 | 0.15 | 0.30 | 0.60 |
| SL-11160 | (structure) .8 HCl | 0.15 | 0.13 | 0.55 | 0.40 |
| SL-11175 | (structure) .14 HCl | 0.32 | 0.24 | 0.35 | 0.5 |
| SL-11226 | (structure) .12 HCl | 0.15 | 0.08 | 0.11 | 0.14 |

Example 14

Cellular Uptake of Oligoamines. There was considerable uptake of oligoamines by the cancer cell lines; see Table 3A (DuPro cells) and Table 3B (PC-3 cells). In most cases, only a minor decrease in intracellular polyamine levels were observed in both cell lines even at conditions where the oligoamines exhibit considerable growth inhibition and cytotoxicity. Therefore, these data suggest that the mechanism of cytotoxicity of oligoamines did not involve depletion of intracellular polyamine pools. While not wishing to be limited by any particular theory of operation, the cytotoxicity is likely related to their strong aggregation effect on DNA.

Polyamine Analysis. An appropriate number of cells were taken from harvested samples and centrifuged at 1000 rpm at 4° C. for 5 min. The cells were washed twice with chilled Dulbecco's isotonic phosphate buffer (pH 7.4) by centrifugation at 1000 rpm at 4° C. and resuspended in the same buffer. After the final centrifugation, the supernatant was decanted, and 250 ml of 8% sulfosalycilic acid was added to the cell pellet. The cells were sonicated, and the mixture was kept at 4° C. for at least 1 h. After centrifugation at 8000 g for 5 min, the supernatant was removed for analysis. An appropriate volume (50-100 μl) was fluorescence-labeled by derivatizing with dansyl chloride. Labeled polyamines were loaded onto a C-18 high-performance liquid chromatography column and separated by gradient elution with acetonitrile/water at 50° C. Peaks were detected and quantitated using Shimadzu HPLC fluorescence monitor coupled with a Spectra-Physics peak integrator. Because polyamine levels vary with environmental conditions, control cultures were sampled for each experiment.

of feeder cells and length of incubation time for observable colony formation. Cells were washed, harvested, and replated in quadruplicate at appropriate dilution into 60 mm plastic Petri dishes. The Petri dishes were prepared not more than 24 hr in advance with 4 ml of supplemented Eagle's minimum essential medium containing 5-10% fetal bovine serum (standardized for each cell line) for all cell lines. Cells were incubated for the previously standardized number of days in a 95% air/5% $CO_2$ atmosphere. The plates were stained with 0.125% crystal violet in methanol and counted. Results are expressed as the surviving fraction of an appropriate control.

TABLE 3A

Cellular Polyamine and Oligoamine levels of DuPro Cells treated with Oligoamines

| Treatment | Analog Conc. (μM) | Polyamine levels (nmoles/$10^6$ cells) on Day 4 of Treatment | | | | Polyamine levels (nmoles/$10^6$ cells) on Day 6 of Treatment | | | |
|---|---|---|---|---|---|---|---|---|---|
| | | Put | Spd | Spm | Analog | Put | Spd | Spm | Analog |
| Control | — | 0.966 | 3.870 | 1.006 | — | 0.567 | 2.930 | 0.680 | — |
| SL-11159 | 0.8 | 0.560 | ND | ND | 0.525 | * | * | * | * |
| | 1.6 | 0.137 | ND | ND | 0.513 | * | * | * | * |
| SL-11160 | 0.8 | 0.430 | 0.897 | 0.222 | 0.575 | 0.675 | 1.470 | 0.290 | 0.410 |
| | 1.6 | 0.412 | ND | 0.195 | 0.775 | * | * | * | * |
| SL-11175 | 0.8 | 0.157 | ND | 0.050 | 0.145 | 0.155 | ND | ND | 0.023 |
| | 1.6 | 0.410 | ND | ND | 0.150 | * | * | * | * |
| SL-11226 | 0.8 | 0.593 | 0.017 | 0.067 | 0.032 | 0.548 | ND | ND | 0.022 |
| | 1.6 | * | * | * | * | * | * | * | * |

ND = Not detected;
* = Cell yield is too low for accurate measurement

TABLE 3B

Cellular Polyamine and Oligoamine levels of PC-3 Cells treated with Oligoamines.

| Treatment | Analog Conc. (μM) | Polyamine levels (nmoles/$10^6$ cells) on Day 4 of Treatment | | | | Polyamine levels (nmoles/$10^6$ cells) on Day 6 of Treatment | | | |
|---|---|---|---|---|---|---|---|---|---|
| | | Put | Spd | Spm | Analog | Put | Spd | Spm | Analog |
| Control | — | 0.567 | 2.790 | 0.660 | — | 0.300 | 0.565 | 0.234 | — |
| SL-11159 | 1 | 0.525 | 0.531 | 0.300 | 0.513 | 0.640 | ND | ND | 1.026 |
| | 5 | 0.670 | ND | 0.240 | 0.388 | * | * | * | * |
| SL-11160 | 1 | ND | 0.097 | 0.502 | 0.005 | ND | 0.085 | 0.180 | 0.007 |
| | 5 | ND | 0.077 | 0.525 | 0.011 | * | * | * | * |
| SL-11175 | 1 | 0.515 | ND | ND | 0.055 | 0.76 | ND | ND | 0.08 |
| | 5 | 0.519 | ND | ND | 0.128 | * | * | * | * |
| SL-11226 | 1 | 0.573 | ND | ND | 0.021 | * | * | * | * |
| | 5 | 0.985 | 0.071 | ND | 0.026 | * | * | * | * |

ND = Not detected;
* = Cell yield is too low for accurate measurement

Example 15

Figure 2:
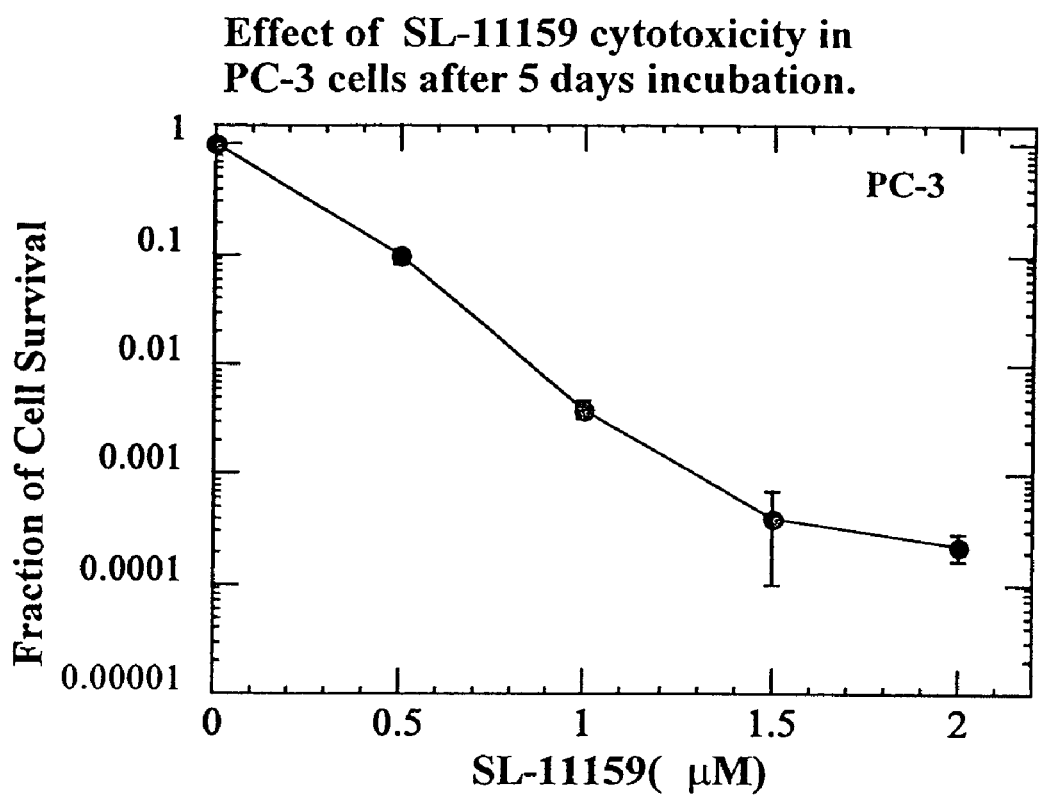
FIG. 2 depicts the effect of SL-11159 cytotoxicity on PC-3 cancer cells after 5 days incubation.

Assessment of Oligoamine Cytotoxicity by Colony Forming Assay. The cytotoxicity of the oligoamines was further assayed by the colony forming assay (CFE). Four saturated oligoamines were chosen for their ability to kill DuPro cells after 5 days of incubation. Oligoamines SL-11159, SL-11175 and SL-11226 had over 4 logs of cell kill on day 5 of treatment at 1-2 μM concentrations; see FIG. 1. Although the prostate tumor PC-3 line was somewhat less susceptible to Oligoamine treatment (see Table 2 of $ID_{50}$ values), a colony survival assay showed that at very low concentrations (ca. 1.5-2 μM) SL-11159 kills almost four logs of PC-3 cells; see FIG. 2. The colony forming assay was performed as follows.

Colony Forming Efficiency Assay. All cell lines used in this assay have already been optimized with respect to the number Example 16

Response of implanted sc DU-145 prostate tumors to treatment with SL-11159 and SL-11226. This experiment evaluates the antitumor efficacy of SLIL Biomedical Corporation compounds (SL-11159, SL-11226) against subcutaneously-implanted DU-145 human prostate tumor xenografts in male NCr-nu (line 3A10F17T1) mice. All compounds were tested at a single dose level when administered intravenously (iv), at 6.25 mg/kg. Both SL-11159 and SL-11226 were prepared in water for injection (soluble); the injection volume was 0.1 mL/10 g body weight.

All compounds were administered for two rounds of five daily treatments with a nine-day rest period between the rounds. The control group was treated with vehicle (water for injection) for two rounds on a Q1D×5 schedule. There were sixteen mice in the control group and eight mice in each of the treatment groups. All treatments were initiated on day 14 postimplant when all mice had established tumors ranging in size from 75 to 198 mg. The experiment was terminated on day 53 after tumor implantation. The individual animal's time to reach the evaluation size (time to reach four doublings) was used in the calculations of the median tumor growth delay [(T−C)/C×100, %] and as the endpoint in a life tables analysis (stratified Kaplan-Meier estimation followed by the Mantel-Haenszel log-rank test) in order to statistically compare the growth data between groups (see Table 5; group 1 is the control group, group 2 was treated with SL-11159, group 3 was treated with SL-11226).

The time required for a tumor to double in mass is calculated based on the initial tumor weight at the beginning of the treatment period. When the initial tumor weight has been selected, tumor weights are then examined, beginning with the last recorded value, until a doubling is calculated. Examination from the last recorded value is to ensure that the doubling time is calculated during the final phase of tumor growth and not prior to a tumor regression. Values between measurements are calculated by exponential extrapolation, and a value may be estimated after the final measured weight provided the extrapolated value occurs prior to the animal's death.)

Control tumors grew well in fourteen out of sixteen mice. There was one xenograft failure (no-take). One animal died during the second round of the vehicle treatment, on day 29, with a tumor weight of 770 mg. Tumors reached the evaluation size of four mass doublings in 17.1 days, which covers the period of the first round of treatment and three days of the second round of treatment. The effect of each round of treatment was evaluated by the comparison of the median tumor weight of the treated groups on days 21 or 35 (three days after the end of the first or the second round of treatment, respectively) to the median tumor weight of the control group on the same day (T/C×100%, see Table 4A).

The first round of SL-11159 treatment was well tolerated without deaths and an average maximum body weight loss of 4% (1 g). The second round of treatment resulted in the death of one animal and a weight loss of 11% (3 g). The treatment resulted in a statistically significant growth delay of >40%. The SL-11226 treatment was well tolerated without deaths and body weight losses ranging from 0 to 10% (0-3 g). The treatment produced statistically significant growth delays of >37%. Additional details are provided in Table 4B.

In summary, the tested compounds, SL-11159 and SL-11226, exhibited measurable antitumor activity at a dosage which was well tolerated.

TABLE 4B

Treatment Results, cont.

| Tumor Regression | | | | | |
|---|---|---|---|---|---|
| Number of Partial | Number of Complete | Duration Med/Range (Days) | Tumor Free Survival/ Total | Days to 4 Doublings | Days Delay (T-C) |
| — | — | — | 1/16* | 17.1 | — |
| 0 | 0 | — | 0/8 | >24.0 | >6.9 |
| 0 | 0 | — | 0/8 | >23.5 | >6.4 |

*one tumor failure

Notes to Tables 4A and 4B:

Nonspecific deaths: a treated, tumored animal was presumed to be a nonspecific death if its day of death was significantly less (p<0.05) than the corresponding day of death in the treated control group and its tumor was less than 400 mg, or if it died with a tumor of 400 mg or less prior to 45 days after the last day of treatment, or with a regressing tumor prior to 15 days after the last day of treatment, or if the treated animal was uniquely specified as a nonspecific death on data input.

Tumor regression was scored (excluding nonspecific deaths), according to the smallest tumor size attained after the beginning of treatment relative to the size at first treatment: partial: <50 percent of its size at 1 st rx, but not complete. complete: tumor becomes unpalpable.

Duration of regression: the interval during which a tumor classified as a partial or complete regressor was below 50 percent of its size at first treatment.

Evaluation size: this value is the tumor mass selected at four mass doublings beginning with the initial tumor size at the start of treatment.

T−C (days): the difference in the median of times postimplant for tumors of the treated groups to attain an evaluation size compared to the median of the control group. The T−C value is measured excluding nonspecific deaths and any other animal that dies whose tumor failed to attain the evaluation size.

TABLE 5

Summary Of The Statistical Analysis

| GROUP PAIRS | P VALUE* |
|---|---|
| 1 vs. 2 | 0.0016 |
| 1 vs. 3 | 0.0082 |

*Mantel-Haenszel Log-Rank Test

TABLE 4A

| | Treatment | | | Treatment Results | | |
|---|---|---|---|---|---|---|
| Group No. | Agent | Dose (mg/kg); [route] | Schedule | % T/C, Day 21 | % T/C, Day 35 | Non-Specific Deaths/ Total |
| 1 | control | — | Q 1D × 5 day 14, 28 | — | — | — |
| 2 | SL-11159 | 6.25 [IV] | Q 1D × 5 day 14, 28 | 65 | 63 | 1/8 |
| 3 | SL-11226 | 6.25 [IV] | Q 1D × 5 day 14, 28 | 46 | 61 | 0/8 |

All references, publications, patents and patent applications mentioned herein are hereby incorporated by reference herein in their entirety.

Although the foregoing invention has been described in some detail by way of illustration and example for purposes of clarity and understanding, it will be apparent to those skilled in the art that certain changes and modifications may be practical. Therefore, the description and examples should not be construed as limiting the scope of the invention, which is delineated by the appended claims.

What is claimed is:

1. A compound of the formula

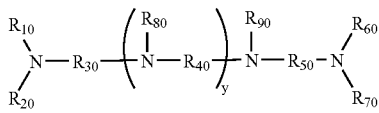

where $R_{10}$ is H, $R_{60}$ is H, $R_{20}$ is ethyl, and $R_{70}$ is ethyl;
each $R_{80}$ and $R_{90}$ are independently selected from H, ethyl, n-propyl, isopropyl, n-butyl, isobutyl, sec-butyl, and t-butyl;
$R_{30}$, each $R_{40}$, and $R_{50}$ are independently selected from:
—CH$_2$CH$_2$CH$_2$CH$_2$—
—CHOHCH$_2$CH$_2$CH$_2$—
—CH$_2$CHOHCH$_2$CH$_2$—
—CH$_2$CH$_2$CHOHCH$_2$—
—CH$_2$CH$_2$CH$_2$CHOH—
—CH$_2$CH$_2$CH$_2$—
—CHOHCH$_2$CH$_2$—
—CH$_2$CHOHCH$_2$— and
—CH$_2$CH$_2$CHOH—;
and where y is an integer selected from 6, 8, 10, 11, 12, and 13;
and all salts thereof.

2. A compound according to claim 1, where each $R_{40}$ is independently selected from the group consisting of —CH$_2$CH$_2$CH$_2$— and —CH$_2$CH$_2$CH$_2$CH$_2$—.

3. A compound according to claim 2, where each $R_{40}$ is —CH$_2$CH$_2$CH$_2$CH$_2$—.

4. A compound according to claim 3, where $R_{30}$ and $R_{50}$ are —CH$_2$CH$_2$CH$_2$CH$_2$—.

5. A compound according to claim 4, where $R_{90}$ and each $R_{80}$ are H.

6. A compound according to claim 5, where y is an integer selected from 11 and 13.

7. A compound according to claim 6, where y is 11.

8. A compound according to claim 1 of the formula

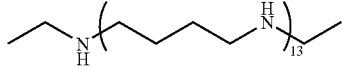

and all salts thereof.

9. A compound according to claim 1, where $R_{90}$ and each $R_{80}$ are independently selected from the group consisting of H and ethyl.

10. A compound according to claim 1, where $R_{90}$ and each $R_{80}$ are H.

11. A compound according to claim 1, where $R_{30}$, each $R_{40}$, and $R_{50}$ are independently selected from:
—CH$_2$CH$_2$CH$_2$CH$_2$—
—CHOHCH$_2$CH$_2$CH$_2$—
—CH$_2$CHOHCH$_2$CH$_2$—
—CH$_2$CH$_2$CHOHCH$_2$—, and
—CH$_2$CH$_2$CH$_2$CHOH—.

12. A compound according to claim 1, where each $R_{40}$ is —CH$_2$CH$_2$CH$_2$CH$_2$— and $R_{30}$ and $R_{50}$ are independently selected from:
—CH$_2$CH$_2$CH$_2$CH$_2$—
—CHOHCH$_2$CH$_2$CH$_2$—
—CH$_2$CHOHCH$_2$CH$_2$—
—CH$_2$CH$_2$CHOHCH$_2$—, and
—CH$_2$CH$_2$CH$_2$CHOH—.

13. A compound according to claim 12, where $R_{30}$ and $R_{50}$ are independently selected from:
—CHOHCH$_2$CH$_2$CH$_2$—
—CH$_2$CHOHCH$_2$CH$_2$—
—CH$_2$CH$_2$CHOHCH$_2$—, and
—CH$_2$CH$_2$CH$_2$CHOH—.

14. A compound according to claim 1, with the proviso that at least one $R_{30}$, $R_{40}$, or $R_{50}$ is independently selected from:
—CHOHCH$_2$CH$_2$CH$_2$—
—CH$_2$CHOHCH$_2$CH$_2$—
—CH$_2$CH$_2$CHOHCH$_2$—
—CH$_2$CH$_2$CH$_2$CHOH—
—CHOHCH$_2$CH$_2$—
—CH$_2$CHOHCH$_2$— and
—CH$_2$CH$_2$CHOH—.

15. A compound according to claim 14, with the proviso that at least one $R_{30}$, $R_{40}$, or $R_{50}$ is independently selected from:
—CHOHCH$_2$CH$_2$CH$_2$—
—CH$_2$CHOHCH$_2$CH$_2$—
—CH$_2$CH$_2$CHOHCH$_2$—; and
—CH$_2$CH$_2$CH$_2$CHOH—.

16. A compound according to claim 15, with the proviso that at least one of $R_{30}$ and $R_{50}$ is independently selected from:
—CHOHCH$_2$CH$_2$CH$_2$—
—CH$_2$CHOHCH$_2$CH$_2$—
—CH$_2$CH$_2$CHOHCH$_2$—; and
—CH$_2$CH$_2$CH$_2$CHOH—.

17. A method of reducing a cancer or the symptoms of a cancer, or retarding the progression of a cancer or of the symptoms of a cancer, in an individual, comprising the step of administering an amount of a compound according to claim 1 sufficient to reduce the cancer or the symptoms of the cancer, or to retard the progression of the cancer or of the symptoms of the cancer.

18. A method of reducing a cancer or the symptoms of a cancer, or retarding the progression of a cancer or of the symptoms of a cancer, in an individual, comprising the step of administering an amount of a compound according to claim 6 sufficient to reduce the cancer or the symptoms of the cancer, or to retard the progression of the cancer or of the symptoms of the cancer.

19. A method of making a compound of the formula

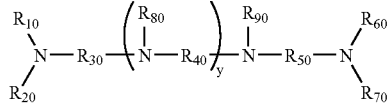

where $R_{10}$ is H, $R_{60}$ is H, $R_{20}$ is ethyl, and $R_{70}$ is ethyl;
each $R_{80}$ and $R_{90}$ are independently selected from H, methyl, ethyl, n-propyl, isopropyl, n-butyl, isobutyl, sec-butyl, and t-butyl;

$R_{30}$, each $R_{40}$, and $R_{50}$ are independently selected from:
—$CH_2CH_2CH_2CH_2$—
—$CHOHCH_2CH_2CH_2$—
—$CH_2CHOHCH_2CH_2$—
—$CH_2CH_2CHOHCH_2$—
—$CH_2CH_2CH_2CHOH$—
—$CH_2CH_2CH_2$—
—$CHOHCH_2CH_2$—
—$CH_2CHOHCH_2$— and
—$CH_2CH_2CHOH$—;
and where y is an integer selected from 6, 8, 9, 10, 11, 12, and 13;
and all salts thereof;
comprising the steps of:
a) providing a first compound of the form

H—N($R_{90}$)-$R_{51}$—CON($R_{60}$)($R_{70}$)

where $R_{90}$ is independently selected from H, methyl, ethyl, n-propyl, isopropyl, n-butyl, isobutyl, sec-butyl, and t-butyl;
$R_{60}$ is H and $R_{70}$ is ethyl;
$R_{51}$ is selected from the group consisting of
—$CH_2CH_2CH_2$—
—$CHO(PG_{Hy})CH_2CH_2$—
—$CH_2CHO(PG_{Hy})CH_2$—
—$CH_2CH_2CHO(PG_{Hy})$—
—$CH_2CH_2$—
—$CHO(PG_{Hy})CH_2$— and
—$CH_2CHO(PG_{Hy})$—;
where $PG_{Hy}$ is a hydroxy protecting group;
b) providing a second compound of the form $BG_N$N($R_{80}$)—$R_{41}$—COOH where blocking group $BG_N$ is selected from the group consisting of an amino protecting group and methyl, ethyl, n-propyl, isopropyl, n-butyl, isobutyl, sec-butyl, and t-butyl;
$R_{41}$ is selected from the group consisting of
—$CH_2CH_2CH_2$—
—$CHO(PG_{Hy})CH_2CH_2$—
—$CH_2CHO(PG_{Hy})CH_2$—
—$CH_2CH_2CHO(PG_{Hy})$—
—$CH_2CH_2$—
—$CHO(PG_{Hy})CH_2$— and
—$CH_2CHO(PG_{Hy})$—;
c) activating the carboxyl group of the second compound;
d) acylating the nitrogen of the first compound with the activated carboxyl group of the second compound to form an amide of the formula $BG_N$[N($R_{80}$)—$R_{41}$—CO]$_g$—N($R_{90}$)—$R_{51}$—CON($R_{60}$)($R_{70}$)

where g is 1;
e) repeating step c) and repeating the coupling step of step d) for (g-1) additional cycles to form a compound of the formula $BG_N$[N($R_{80}$)—$R_{41}$—CO]$_g$—N($R_{90}$)—$R_{51}$—CON($R_{60}$)($R_{70}$)
where g is an integer from 7 to 15;
f) reducing the amide groups to amine groups; and
g) removing any protecting groups $BG_N$ and $PG_{Hy}$ that may be present in the compound.

20. A compound of the formula $$\begin{array}{c} R_{10} \\ \diagdown \\ N-R_{30}-\left(\begin{array}{c} R_{80} \\ | \\ N-R_{40} \end{array}\right)_y \begin{array}{c} R_{90} \\ | \\ N-R_{50}-N \end{array} \diagup R_{60} \\ \diagup \\ R_{20} \end{array} \diagdown R_{70}$$

where $R_{10}$ is H, $R_{60}$ is H, $R_{20}$ is ethyl, and $R_{70}$ is ethyl;
each $R_{80}$ and $R_{90}$ are independently selected from H, ethyl, n-propyl, isopropyl, n-butyl, isobutyl, sec-butyl, and t-butyl;
$R_{30}$, each $R_{40}$, and $R_{50}$ are independently selected from:
—$CH_2CH_2CH_2CH_2$—
—$CHOHCH_2CH_2CH_2$—
—$CH_2CHOHCH_2CH_2$—
—$CH_2CH_2CHOHCH_2$—
—$CH_2CH_2CH_2CHOH$—
—$CH_2CH_2CH_2$—
—$CHOHCH_2CH_2$—
—$CH_2CHOHCH_2$— and
—$CH_2CH_2CHOH$—;
and where y is 9;
and all salts thereof.

21. A compound according to claim 20 of the formula $$\diagup\diagdown_{\underset{H}{N}}\diagdown\diagdown\diagdown\diagup\left(\diagdown\diagdown\diagdown\diagup\underset{H}{\overset{H}{N}}\diagdown\right)_{11}$$

and all salts thereof.

* * * * *